(12) United States Patent
Kruse et al.

(10) Patent No.: US 7,820,177 B2
(45) Date of Patent: Oct. 26, 2010

(54) SELF-ADHESIVE POLYMER MATRIX CONTAINING A SEAWEED EXTRACT

(75) Inventors: Inge Kruse, Hamburg (DE); Rainer Wolber, Hamburg (DE); Karl-Heinz Woeller, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1321 days.

(21) Appl. No.: 11/157,946

(22) Filed: Jun. 22, 2005

(65) Prior Publication Data

US 2005/0281869 A1 Dec. 22, 2005

Related U.S. Application Data

(63) Continuation of application No. PCT/EP03/14792, filed on Dec. 23, 2003.

(30) Foreign Application Priority Data

Dec. 23, 2002 (DE) .................. 102 60 872

(51) Int. Cl.
A61K 36/02 (2006.01)
A61K 9/14 (2006.01)
A61K 9/70 (2006.01)
(52) U.S. Cl. .................. 424/195.17; 424/487; 424/449
(58) Field of Classification Search .................. None
See application file for complete search history.

(56) References Cited

U.S. PATENT DOCUMENTS

| | | |
|---|---|---|
| 3,770,780 A | 11/1973 | Hirsch |
| 3,790,533 A | 2/1974 | Samour |
| 3,900,610 A | 8/1975 | McKenna, Jr. |
| 4,144,325 A | 3/1979 | Voyt |
| 4,248,861 A | 2/1981 | Schutt |
| 4,369,180 A | 1/1983 | Mihalovits |
| 4,978,531 A | 12/1990 | Yamazaki et al. |
| 5,094,761 A | 3/1992 | Trinh et al. |
| 5,102,564 A | 4/1992 | Gardlik et al. |
| 5,194,253 A | 3/1993 | Garrido |
| 5,234,610 A | 8/1993 | Gardlik et al. |
| 5,324,718 A | 6/1994 | Loftsson |
| 5,472,954 A | 12/1995 | Loftsson |
| 5,543,157 A | 8/1996 | Trinh et al. |
| 5,552,378 A | 9/1996 | Trinh et al. |
| 5,571,782 A | 11/1996 | Trinh et al. |
| 5,580,851 A | 12/1996 | Trinh et al. |
| 5,635,238 A | 6/1997 | Trinh et al. |
| 5,660,845 A | 8/1997 | Trinh et al. |
| 5,773,029 A | 6/1998 | Chiesi et al. |
| 5,827,529 A | 10/1998 | Ono et al. |
| 6,190,689 B1 | 2/2001 | Hoffmann et al. |
| 6,217,913 B1* | 4/2001 | Mohammadi ............... 424/520 |
| 6,300,377 B1* | 10/2001 | Chopra ....................... 514/715 |
| 6,419,935 B1 | 7/2002 | Gueret |
| 6,572,868 B1* | 6/2003 | Cope ........................ 424/400 |
| 2001/0007671 A1 | 7/2001 | Gueret |
| 2002/0034525 A1 | 3/2002 | Sakai et al. |
| 2002/0076387 A1 | 6/2002 | Birkel et al. |
| 2002/0150616 A1 | 10/2002 | Vandecruys |

FOREIGN PATENT DOCUMENTS

| | | |
|---|---|---|
| DE | 6 8915737 | 3/1990 |
| DE | 1 9646233 | 5/1997 |
| DE | 1 0051955 | 5/2002 |
| DE | 1 0054479 | 5/2002 |
| EP | 1172083 | 1/1970 |
| EP | 0303445 | 2/1989 |
| EP | 0392608 | 10/1990 |
| EP | 0507160 | 10/1992 |
| EP | 0579435 | 1/1994 |
| EP | 0976382 | 2/2000 |
| EP | 0756493 | 7/2000 |
| EP | 1136057 | 9/2001 |
| FR | 94777 | 2/1970 |
| FR | 2808195 | 11/2001 |
| JP | 63-208518 | 8/1988 |
| JP | 2-243607 | 9/1990 |
| JP | 4-178323 | 6/1992 |
| JP | 11-228340 | 8/1999 |
| RU | 2158125 | 10/2000 |
| WO | 95/30411 | 11/1995 |
| WO | 98/55148 | 12/1998 |
| WO | 01/02478 | 1/2001 |

OTHER PUBLICATIONS

DW ACC 1988-283016, Aug. 1988, DW or JP, Kumazawa et al.*
U.S. Appl. No. 11/157,959, filed Jun. 22, 2005 and entitled "Self-Adhesive Polymer Matrix Containing a Sea Algae Extract and Glycerin".
English language Abstract of DE 100 54 479.
English language Abstract of RU 2158125.
English language Abstract of FR 2808195.

(Continued)

Primary Examiner—Christopher R Tate
Assistant Examiner—Randall Winston
(74) Attorney, Agent, or Firm—Greenblum and Bernstein, P.L.C.

(57) ABSTRACT

A self-adhesive polymer matrix which comprises a polymer that forms a gel in water, water, a sea algae extract, and a monohydric or polyhydric alcohol.

22 Claims, No Drawings

OTHER PUBLICATIONS

English language Abstract of DE 19646233.
English language Abstract of JP 06304239 and English language machine translation of JP 06304239.
English language Abstract of 11-228340.
English language Abstract of 4-178323.
Deflandre A. et al. "Photostability Assessment of Sunscreens. Benzylidene Camphor and Dibenzoylmethane Derivatives" International Journal of Cosmetic Science, vol. 10, 1988, pp. 53-62.
Voelckel A. et al. "Vorkommen und Photo-Isomerisierung der Urocaninsäure im Stratum Corneum bei polymorpher Lichtdermatose (PLD). Vergleichende Untersuchung bei PLD-Patienten und Hautgesunden" Zentralblatt Haut- und Geschlechtskrankheiten, Springer-Verlag, vol. 156, 1989, pp. 1-15.
Miyachi Y. "Skin Diseases Associated with Oxidative Injury" in "Oxidative Stress in Dermatology", edited by Fuchs J., Packer L., Marcel Dekker, Inc. New York, Basel, Hong Kong, 1993, pp. 323-331.
Zviak C. "Hair Coloring-Nonoxidation Coloring" and "Oxidation Coloring" in "The Science of Hair Care", Marcel Dekker, Inc., 1986, pp. 235-286.
Elias P. M. "Structure and Function of the Stratum Corneum Permeability Barrier" Drug Development and Research, vol. 13, 1988, pp. 97-105.
Quecke K. "Transdermale therapeutische Systeme und ihre Klebstoffproblematik" Kleben & Dichten, Jhrg. 42 (1998), No. 5, p. 26-30.
Donatas Satas "Handbook of Pressure Sensitive Adhesive Technology" $3^{rd}$ ed. (1999), Satas & Associates, Warwick, RI, pp. 458-461.
Uekama K. et al. "Cyclodextrin Drug Carrier Systems" Chemical Reviews, 1998, vol. 98, pp. 2045-2076.
Loftsson T. et al. "Cyclodextrins: New Drug Delivery Systems in Dermatology" International Journal of Dermatology, 1998, vol. 37., pp. 241-246.
Motwani M. et al. "Applications of Cyclodextrins in Skin Products" Cosmetics & Toiletries, vol. 112, Jul. 1997, pp. 39-47.
Citernesi U. et al. "Cyclodextrins in Functional Dermocosmetics" Cosmetics & Toiletries, vol. 110, Mar. 1995, pp. 53-61.
Wallhäusser K. H. "Praxis der Sterilisation Desinfektion—Konservierung" $5^{th}$ ed., 1995, Georg Thieme Verlag, Stutgart, New York, pp. 469-474.
English Language Abstract of JP 2-243607.
English Language Abstract of JP 63-208518.

* cited by examiner

SELF-ADHESIVE POLYMER MATRIX CONTAINING A SEAWEED EXTRACT

CROSS-REFERENCE TO RELATED APPLICATIONS

The present application is a continuation of International Application No. PCT/EP2003/014792, filed Dec. 23, 2003, the entire disclosure whereof is expressly incorporated by reference herein, which claims priority under 35 U.S.C. §119 of German Patent Application No. 102 60 872.5, filed Dec. 23, 2002.

BACKGROUND OF THE INVENTION

1. Field of the Invention

The present invention relates to a self-adhesive polymer matrix composed of a polymer which is gel-forming in water, preferably a polyacrylic acid polymer, water, sea algae extract, and a monohydric or polyhydric alcohol. The matrix may be doped with hydrophilic or else hydrophobic active substances. The choice of active substance or substances is made in accordance with the field of application, which is a function of the particular requirements of the skin.

2. Discussion of Background Information

The skin is exposed to continually changing environmental effects and is also subject over time to a series of changes. For instance, as described below, there are changes in the barrier properties, in skin creasing and elasticity, in pigmentation, examples being age spots or abnormal pigmentations such as melasma and the like, and in particular, as a result of exogenous influences, there are also various inflammatory reactions, reactions of the skin subsequent to exposure to UV radiation, i.e., sunburn, and/or irritation as a result of shaving.

As well as the positive effects of sunlight, such as general well-being, the formation of vitamin D3 and the treatment of acne, there are also negative effects, which must be countered.

The damaging effect of the ultraviolet fraction of solar radiation on the skin is general knowledge. Whereas radiation of a wavelength of less than 290 nm, known as the UVC region, is absorbed by the ozone layer in the earth's atmosphere, radiation in the region between 290 nm and 320 nm, known as the UVB region, causes erythema, simple sunburn or even more or less severe burns on the skin.

Numerous compounds are known for protecting against UVB radiation, and are generally derivatives of 3-benzylidenecamphor, of 4-aminobenzoic acid, of cinnamic acid, of salicylic acid, of benzophenone, and of 2-phenylbenzimidazole.

Approximately 90% of the ultraviolet radiation reaching the Earth is composed of UV-A rays with a wavelength between 320 nm and 400 nm. Whereas the UV-B radiation varies greatly depending on numerous factors, e.g., season, time of day or latitude, the UV-A radiation remains relatively constant day by day, independently of seasonal, time-of-day or geographical factors. At the same time the predominant fraction of UV-A radiation penetrates the living epidermis, whereas about 70% of the UV-B rays are retained by the horny layer.

In order to protect against the rays of the UVA region, therefore, certain derivatives of dibenzoylmethane are used, whose photostability (Int. J. Cosm. Science 10, 53 (1988)) is inadequate.

For a long time it was erroneously assumed that the long wave UV-A radiation only has a negligible biological effect and that, accordingly, it is the UV-B rays that are responsible for the majority of photodamage to the human skin. In the meantime, however, numerous studies have demonstrated that UV-A radiation is far more dangerous than UV-B radiation with regard to the triggering of photodynamic reactions, especially phototoxic reactions, and chronic changes to the skin. Thus it has emerged that UV-A radiation leads to damage to the elastic and collagenic fibers of the connective tissue, causing the skin to age prematurely. Here, elasticity and water storage capacity of the skin are reduced, i.e., the skin becomes less smooth and tends to form wrinkles. This kind of wrinkling is also referred to as light-induced skin aging. The markedly high incidence of skin cancer in places with high insolation shows that, evidently, damage to the inherited information in the cells is also brought about by sunlight. Moreover, the damaging effect of UV-B radiation can be further intensified by UV-A radiation.

Since the contribution of the different wavelength ranges of UV light to light-induced skin aging have not been fully elucidated, it is increasingly assumed nowadays that preventive protection both against UV-A rays and against UV-B rays, through the application, for example, of sunscreen substances to the skin in the form of a cosmetic or dermatological formulation, is of fundamental importance. Cosmetic or dermatological compositions ought, when applied to the skin in a thin layer, to protect it against the adverse consequences of solar radiation.

UV radiation, however, can also, as noted above, lead to photochemical reactions, with the photochemical reaction products then intervening in the skin's metabolism.

Photochemical reaction products of this kind are predominantly free-radical compounds, examples being hydroxyl radicals. Undefined free-radical photo products as well, formed in the skin itself, may manifest uncontrolled secondary reactions, owing to their high reactivity. But singlet oxygen as well, a non-radical excited state of the oxygen molecule, can occur under UV radiation, as can short-lived epoxides and many others. Singlet oxygen, for example, is distinguished from the triplet oxygen that is normally present (free-radical ground state) by its increased reactivity. However, there are also excited, reactive (free-radical) triplet states of the oxygen molecule. Processes of this kind, via oxidative damage to various skin structures, play a very substantial role in light-induced skin aging (including wrinkling).

Furthermore, UV radiation is an ionizing radiation. There is therefore a risk of ionic species forming under UV exposure, these species then having the capacity to intervene, themselves, oxidatively in the biochemical processes.

In order to prevent these reactions, additional antioxidants and/or free-radical scavengers can be incorporated into the cosmetic and/or dermatological formulations.

The use of vitamin E, a substance having a known antioxidative effect in sun protection formulations, has already been proposed, but the effect achieved here also remains a long way behind the hoped-for effect.

It was therefore an object of the invention to provide active cosmetic, dermatological, and pharmaceutical substances in preparations and also sun protection formulations which serve for the prophylaxis and treatment of light-sensitive skin, especially photodermatoses, preferably polymorphic photodermatosis.

Further terms for polymorphic photodermatosis are PLD, PLE, Majorca acne, and a host of further designations, as reported in the literature (e.g., A. Voelckel et al., Zentralblatt Hautund Geschlechtskrankheiten (1989), 156, p. 2).

Antioxidants are used principally as substances for protection from the spoiling of the preparations comprising them. It is nevertheless known that in human and animal skin, as well, unwanted oxidation processes may occur.

The essay "Skin Diseases Associated with Oxidative Injury" in "Oxidative Stress in Dermatology", p. 323 ff. (Marcel Decker Inc., New York, Basle, Hong Kong, editors: Jürgen Fuchs, Frankfurt, and Lester Packer, Berkeley, Calif.) sets out oxidative damage to the skin and its more precise causes.

For the purpose of preventing such reactions, as well, antioxidants and/or free-radical scavengers may be additionally incorporated into cosmetic or dermatological formulations.

Certain antioxidants and free-radical scavengers are known. Thus it has already been proposed, in U.S. Pat. Nos. 4,144,325 and 4,248,861, and from numerous other documents, to use vitamin E, a substance with a known antioxidative effect, in sun protection formulations; nevertheless, here again, the effect achieved remains a long way behind that hoped for.

It would be advantageous to find ways to avoid the disadvantages of the prior art. In particular it would be desirable that the effect of the elimination of the damage caused by environmental noxae and the prophylaxis are durable, sustained and without the risk of side effects.

Remedying these deficiencies would be desirable.

Sunbathing is perceived by the majority of people as being pleasurable, and the deleterious consequences are not considered to start with. In recent years, however, an awareness has certainly developed of the adverse consequences of excessively intensive solar irradiation, and so the use of more strongly protecting sun protection compositions is on the increase. Sunburn or photoerythema represents the acute manifestations of exposure to light. As well as the effects of UV rays, which have already been described, a secondary reaction of the skin results, further, in reduced production of sebum and in the skin drying out. In order to alleviate and care for light-ravaged skin, therefore, specific active substances can be used, such as, for example fat restoratives and moisturizers, inflammation-alleviating and cooling substances, local-anesthetic substances and/or disinfectant substances, in order to prevent possible skin infections.

As described before, after a latency period of from 2 to 3 hours, a reddening of the skin occurs which is strongly demarcated from the unirradiated skin—this reddening being called erythema solare—if the skin is exposed to the sun or an artificial radiation source for too long. The sunburn which has arisen in this way is differentiated as follows 1st degree: erythema (reddening, sensation of warmth) subsides after 2 to 3 days and disappears with a simultaneous increase in pigmentation, 2nd degree: blistering blisters form on the skin with burning and itching, and areas of the epidermis are shed, 3rd degree: cell damage deep-down cell damage occurs, the body reacts with fever, extensive areas of the epidermis are shed.

The 2nd and 3rd degrees are also referred to as dermatitis solare.

The formation of erythema is dependent on wavelength. The erythema region of UV-B is between 280 nm and 320 nm. The narrower range around 308 nm is stated as a maximum for the erythema activity of sunlight.

The purpose of what are called aftersun products is to cool the skin after sunbathing and to improve its moisture retention capacity, with the imparting of the cooling effect playing a central part. This cooling effect is generally achieved by high quantities of ethanol, which evaporates spontaneously when the formulation is spread over the skin.

A disadvantage of these prior art formulations, however, is that long-term cooling cannot be achieved, since the ethanol evaporates very rapidly and the resultant cooling effect, accordingly, is of only short duration.

The prior art knows further preparations which, when applied to the skin or mucous membranes, are intended to have a moistening and cooling effect. The literature, for example, describes ionic compounds, especially ammonium salts, as cooling agents. Also in widespread use as cooling preparations are isopropanolic gels with added camphor and added menthol, and, very frequently, essential oils, principally camphor and menthol, but also derivatives thereof, e.g., menthyl lactate or menthyl 3-hydroxybutyrate, are incorporated into cooling compositions.

Menthol, camphor and derivatives thereof, and also other essential oils, lower the sensitivity threshold of the neuronal cold receptors and so bring about a sensation of coldness. In many cases, however, at the same time they produce an increase in circulation, which, in contrast, induces a sensation of heat. The use of these substances, particularly on irritated skin, is in any case problematical. Furthermore, many of these compounds have a poor water-solubility. Their use is consequently limited to a few cosmetics and dermatological products.

It would be desirable, therefore, to find cosmetic or dermatological preparations which do not exhibit the disadvantages of the prior art and which provide long-lasting care in particular to light-ravaged skin.

In adolescent men, the growth of beard hair is triggered by the increased formation of male hormones during puberty. Hormonal disorders in women can also lead to a form of beard growth, but its extent generally remains a long way behind that of male beard growth.

Shaving of the face or other parts of the body with hair growth, such as the legs, armpits or genital area, for example, may be motivated by a variety of impulses—of religious or cultural nature, for example; at its most simple, hair growth is unwanted by the person concerned simply on cosmetic grounds.

Shaving is carried out either dry or wet. The development of new mechanical and electrical wet and dry shaving technologies makes it possible nowadays to remove (beard) hair reliably and thoroughly. For wet shaving, chemical auxiliaries—in the form, for example, of shaving gels, shaving soaps or shaving foams—are generally vital. They are needed in order to soften the (beard) hair and so to minimize the application of force required in order to sever them—and hence to minimize the unpleasant pulling on the shaft of the hair. The softening of the (beard) hairs is achieved by absorption of water, which is made possible by the increase in the pH of the hairs. Wet shaving products therefore generally contain soaps or fatty acid salts whose pH is situated in the range 8-10. Products for wet shaving therefore produce a typical skin sensation which arises after application. The skin is dry and rough to the touch. This skin sensation is also referred to within the cosmetics art as "squeaky feeling", and is extremely unpopular among consumers both male and female.

In the case of dry shaving as well, cosmetic products are frequently advisable in order to produce as close a shave as possible, i.e., to cut off the (beard) hair as close as possible to the skin surface.

The areas of the skin affected by shaving may, however, be not only irritated by the shaving auxiliaries; the mechanical irritation caused by shaving per se constitutes a burden on the skin, and may result in an unpleasant skin sensation, referred to as "shaving burn".

It would therefore also be desirable to provide cosmetic or dermatological preparations which better alleviate the secondary reactions of the skin to (mechanical) irritation as a result of shaving.

The pigmentation of human skin is produced essentially by the presence of melanin. Melanin and its degradation products, carotene, degree of perfusion, and the condition and thickness of the Stratum corneum and other skin layers cause the appearance of skin shades ranging from virtually white, in the event of reduced filling or absence of the blood vessels, or yellowish via light brown-reddish, bluish to brown of different shades and finally almost black. The individual regions of the skin display different depths of shading as a result of different amounts of melanin.

Natural melanin protects the skin against penetrating UV radiation. The number of melanin granules produced in the melanocytes determines whether the skin is light or dark. In the case of strong pigmentation, as in colored people, for example, but also in pale skinned people after some UV irradiation, melanin is found in the Stratum spinosum and even in the Stratum corneum as well. It attenuates the UV radiation by up to about 90% before the latter reaches the corium.

Responsible for the pigmentation of the skin are the melanocytes, which are found in the bottom-most layer of the epidermis, the Stratum basale, alongside the basal cells, as pigment-forming cells which, depending on skin type, occur either in isolation or else in greater or lesser accumulation. Melanocytes contain, as characteristic cell organelles, melanosomes, in which the melanin is formed. On excitation by UV radiation, among other factors, the formation of melanin is increased. It is transported via the living layers of the epidermis (keratinocytes) ultimately to the horny layer (corneocytes) and induces a more or less pronounced brownish to brown-black skin color. Melanin is formed as the final stage in an oxidative process in which tyrosine, with the assistance of the enzyme tyrosinase, converts via a number of intermediate stages to the brown to brown-black eumelanins, DHICA and DHI melanin, and/or, with the participation of sulfur-containing compounds (cysteine), to the reddish pheomelanin. DHICA and DHI melanin are formed via the common intermediate stages of dopaquinone and dopachrome. The latter is converted, in some cases with participation of further enzymes, either into indole-5,6-quinone-carboxylic acid or into indole-5,6-quinone, from which the two aforementioned eumelanins are formed. Pheomelanin is formed, inter alia, via the intermediates dopaquinone and cysteinyldopa.

Besides various functions of the melanin endogenous to the skin, including "detoxification"/binding of toxic substances/pharmaceuticals, etc., the function of melanin as a natural UV filter to protect against harmful UV rays, and also the antioxidant function of melanin as a protection against reactive oxygen species (oxidative stress), which may arise as a result of solar radiation, among other factors, is very important for the skin, with regard, among other things, to homeostasis, prevention of skin aging, prevention of sunburn, and so on. Hence there should be not only a cosmetic benefit in the sense of enhanced tanning as a result of the increased synthesis of melanin in the skin following topical application of compounds which increase melanogenesis, but also an additional protection as a result of the various protective functions of melanin.

Depending on their sensitivity to light, the following skin types are generally distinguished:
Skin type I never tans, always burns.
Skin type II hardly tans, burns easily.
Skin type III tans averagely well.
Skin type IV tans easily and lastingly, almost never burns.
Skin type V dark, often almost black skin, never burns.

The natural shielding against harmful UV radiation is a tangible advantage of natural skin tanning. For a number of decades now, moreover, a "healthy" skin color has been seen as a sign of sporting activity, in particular, and is therefore regarded by a broad stratum of consumers to be desirable. Representatives of skin types I and II who wish to enjoy such skin shading are therefore driven in any case to rely on self-tanning products. However, representatives of skin type III as well, who wish not to be exposed excessively to the risks of sunbathing but nevertheless want to appear tanned, are appreciative target groups for self-tanning preparations.

The easiest way of giving one's skin a brown shade is to apply appropriately colored make-up products. Naturally, however, the only parts of the body colored are those covered by the colored products. With the aid of make-up products which can be removed by washing it is possible to achieve a slight skin coloring: for example, extracts of fresh green walnut shells, and henna. One disadvantage of the make-ups is therefore the time-consuming process of their application. A further disadvantage is that they strongly stain textiles such as shirt collars or blouses. Furthermore, the various dyes may have different allergenic potential and may even have an irritant effect on the skin.

Artificial skin tanning can be brought about by cosmetic or medicinal means, with the following approaches essentially playing a part:

The regular intake of carotene products results in carotene being stored in the subcutaneous fatty tissue, and the skin gradually turns orange to yellow-brown.

Coloring can also be accomplished by the route of a chemical change in the horny layer of the skin using what are known as self-tanning preparations. The principal active substance is dihydroxyacetone (DHA). The skin tanning achieved in this way cannot be removed by washing and comes off only with the normal flaking of the skin, after about 10-15 days. Dihydroxyacetone can be referred to as ketotriose and, as a reducing sugar, reacts with the amino acids of the skin and with the free amino and imino groups of keratin via a series of intermediate stages, in a Maillard reaction, to form brown-colored substances, referred to as melanoids, which are occasionally also called melanoidins.

A particular disadvantage of tanning with dihydroxyacetone is that, unlike "sun-tanned" skin, the skin tanned with DHA is not protected from sunburn.

A further disadvantage of dihydroxyacetone is that, particularly under the effect of ultraviolet radiation, it gives off formaldehyde, albeit in amounts which are usually small. There was therefore an urgent need to demonstrate ways in which the decomposition of dihydroxyacetone can be effectively countered.

In a further preferred embodiment the present invention relates to cosmetic and dermatological preparations for the prophylaxis and treatment of cosmetic or dermatological skin changes, such as, for example, unwanted pigmentation, examples being local instances of hyperpigmentation and abnormal pigmentation, such as liver spots, freckles, for example, the inhibition of natural pigmentation, or else for the purely cosmetic lightening of relatively large areas of skin which are quite appropriately pigmented for the individual skin type.

Problems with hyperpigmentation of the skin have a wide variety of causes and are phenomena which accompany numerous biological processes, such as UV radiation, for example, e.g., freckles, ephelides, genetic disposition, abnormal pigmentation of the skin in wound healing or scarring, or skin aging, e.g., age spots, lentigines seniles. Age spots and irregular pigmentation of the human skin are the consequence in particular—according to the current state of knowledge—of continual solar UV irradiation and occur to an increased extent, as the name age spot suggests, with age. With age spots there is generally a local increase in the number of pigment-producing cells, the melanocytes, roughly a doubling of the number of melanocytes in comparison with the skin surrounding the age spots. As a result there is also increased pigmentation: the amount of melanin (pigment) increases in the area of the age spots.

Active substances and preparations which counteract skin pigmentation are known. In practice, use is made essentially of products based on hydroquinone, although on the one hand these products only exhibit their effect after a number of weeks of application and, on the other hand, their application for an excessively long time is objectionable on toxicological grounds. The inhibition of tyrosinase with substances such as kojic acid, ascorbic acid and azelaic acid and also derivatives thereof is also common, but has cosmetic and dermatological drawbacks.

Remedying these deficiencies would also be desirable.

In cosmetology, as well as skin health and skin care, hair care is another area of extremely intensive research.

Hair is the thread-like skin appendage which consists of keratin and is almost universal, though absent from the palms of the hand, soles of the feet, extensor sides of the distal phalanges of the toes and fingers; it is differentiated as long hair (head hair, beard hair, axilla hair, pubic hair—capilli, barba, hirci and pubes, respectively; in men also chest hair), short hair, bristle hair (supercilia, cilia, vibrissae, tragi) and down (lanugo, velus hair). The structure of all of these types of hair is similar on the whole: centrally there is the hair medulla (comprising epithelial cells with eosinophilic horny substance granules=trichohyalin granules), surrounded by the hair cortex (comprising keratinized cells; contains pigments) and the outer skin of the hair (cuticular pili; anuclear epidermis layer) and also by layers of the epithelial and connective-tissue hair sheath.

The hair is divided into the hair shaft, protruding from the skin, and the inclined hair root, reaching into the subcutis, whose layers correspond approximately to those of the epidermis. The thickened lower root end, the hair bulb, sits on a vascular pin of connective tissue, the hair papilla, protruding into it (both as hair base). The bulb in the starting phase (=anagen phase) of hair formation, which is repeated cyclically, is coated in the manner of an onion as a result of continual formation of new cells by its layer near the papilla (matrix), then is later closed, bulblike and entirely keratinized (bulb hair), and finally, in the end phase (=telogen phase), is displaced in the direction of the folicular aperture by a new hair, starting from a newly formed hair papilla.

The substance responsible for individual hair color is melanin. Melanin is formed in the melanocytes, cells which occur in the hair bulb in association with the keratinocytes of the hair medulla. Melanocytes contain melanosomes, as characteristic cell organelles, in which the melanin is formed. The melanin is transferred via the long dendrites of the melanocytes into the keratinocytes of the precortical matrix, and brings about the more or less pronounced blond to brown-black hair color.

Eumelanin is the black-brown pigment. It determines primarily the depth of color of the hair. In brown and black hair it occurs in clearly visible granules.

Pheomelanin is the red pigment, it is responsible for pale blond, blond, and red hair. In terms of its structure, this melanin is very much finer and smaller. The various fractions of the types of melanin give rise to the different colors of hair:

blond hair contains a small amount of eumelanin and a large amount of pheomelanin, dark hair contains a large amount of eumelanin and a small amount of pheomelanin, red hair likewise has little eumelanin and a great amount of pheomelanin, all shades of hair in between result from different proportions in which the two types of melanin are mixed.

The process of pigment formation can only proceed if sufficient tyrosinase is available. This enzyme is formed more infrequently with increasing age. This then results, gradually, in gray hair. The reason is as follows: with little tyrosinase, less and less tyrosine as well is formed. Hence the production of melanin also goes down. The absent melanin is replaced by the inclusion of air bubbles. The hair appears gray.

This process is generally insidious. It begins at the temples and then extends to the entire head hair system. Subsequently it affects the beard and the eyebrows. Finally, all of the hair on the body is gray.

Gray hair is referred to medically as canities. There are various possibilities for graying. Premature graying, from age 20, is also known as canities praecox.

Canities symptomatica, or symptomatic graying of the hair, can have a variety of causes. These include:

pernicious anemia (vitamin B deficiency anemia), severe endocrinological disorders, e.g., in the case of thyroid diseases, acute febrile illnesses, drug side-effects cosmetics, metals.

The coloring of hair, in particular of living human hair, using natural dyes, has been known since antiquity, particularly for the dye henna, and which for some years has been pushed into the background in favor of synthetic dyes, has for some years been the object of a new interest. The red shade which arises as a result of henna is a disadvantage.

Melanin production, which causes the hair color, decreases with increasing age: the hair becomes gray or white. For some consumers it is a cosmetic desire to reverse or slow down this process. For this purpose, the cosmetics industry in some countries uses lead acetate, which is toxic and therefore prohibited in the European Cosmetics Directive. This lead acetate is applied preferably in the form of a solution to the hair, where it remains for a prolonged period without being washed off.

For the dyeing of keratin-containing fibers, e.g. hair, wool or furs, use is made generally either of direct dyes or of oxidation dyes, which are formed by oxidative coupling of one or more developer components with one another or with one or more coupler components. Coupler and developer components are also referred to as oxidation dye precursors.

Developer components used are usually primary aromatic amines with a further free or substituted hydroxyl or amino group in the para or ortho position, diaminopyridine derivatives, heterocyclic hydrazones, 4-aminopyrazolone derivatives, and 2,4,5,6-tetra-aminopyrimidine and its derivatives.

Specific representatives are, for example p-phenylenediamine, p-tolylenediamine, 2,4,5,6-tetraminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy- 4,5,6-triaminopyrimidine, 2,4-dihydroxy-5,6-diaminopyrimidine, and 2,5,6-triamino-4-hydroxypyrimidine.

Coupler components used are generally m-phenylenediamine derivatives, naphthols, resorcinol and resorcinol derivatives, pyrazolones, and m-aminophenols. Particularly suitable coupler substances include α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol, and 5-methylresorcinol.

With regard to further customary dye components, reference is made expressly to the series "Dermatology", published by Ch. Culnan, H. Maibach, Verlag Marcel Dekker Inc., New York, Basle, 1986, vol. 7, Ch. Zviak, The Science of Hair Care, chap. 7, pages 248-250 (direct dyes) and chap. 8, pages 264-267 (oxidation dyes), and also the "European Inventory of Cosmetics Raw Materials", 1996, published by the European Commission, available in disk form from the Bundesverband der deutschen Industrieiund Handelsunternehmen für Arzneimittel, Reformwaren und Köperpflegemittel e.V., Mannheim.

Although intense colorations with good fastness properties can be achieved with oxidation dyes, the development of the color takes place generally under the influence of oxidizing agents such as $H_2O_2$, for example, which in certain cases can result in damage to the fiber. Furthermore, certain oxidation dye precursors or particular mixtures of oxidation dye precursors may occasionally have a sensitizing effect in people with sensitive skin. Direct dyes are applied under relatively gentle conditions, but their disadvantage is that the colorations frequently have only inadequate fastness properties.

It would be desirable to improve the independent production of melanin by the hair, but without resort to coloring agents and, in particular, oxidizing agents such as $H_2O_2$, for example. Furthermore, the compositions should have very little sensitization potential, if any at all.

The Elias skin model, which is currently recognized in the art (P. M. Elias, Structure and Function of the Stratum Corneum Permeability Barrier, Drug Dev. Res. 13, 1988, 97-105) describes the horny layer as a two-component system, similar to a brick wall (bricks and mortar model). In this model the horny cells (corneocytes) correspond to the bricks, and the lipid membrane in the intercellular spaces, which is of complex composition, corresponds to the mortar. This system is essentially a physical barrier to hydrophilic substances, but, because of its narrow and multilayered structure, can also be passed only with difficulty by lipophilic substances as well. The particular structure of the horny layer on the one hand protects the skin and on the other hand stabilizes its own flexibility by binding a defined amount of water.

Mechanical stresses as well, such as compressive forces, impact forces or shear forces, for example, can be intercepted to a surprising degree by the horny layer on its own or in conjunction with the deeper layers of the skin. Relatively large compressive, torsional or shear forces are transmitted to deeper layers of the skin via the intermeshing of the epidermis with the corium.

The regulation of the water content and moisture content is one of the most important functions of the epidermal lipid membrane. However, it not only has a barrier effect to external chemical and physical influences, but also contributes to the cohesion of the horny layer.

The lipids of the horny layer consist essentially of ceramides, free fatty acids, cholesterol and cholesterol sulfate, and are distributed throughout the horny layer. The composition of these lipids is of decisive importance for the intact function of the epidermal barrier and hence for the impermeability of the skin to water.

Even cleansing of the skin with a simple water bath—without the addition of surfactants—initially causes the horny layer of the skin to swell. The degree of this swelling depends, among other factors, on the duration of the bath and its temperature. At the same time, water-soluble substances are washed off or out, such as water-soluble dirt constituents, for example, but also substances endogenous to the skin which are responsible for the water-binding capacity of the horny layer. In addition, as a result of surface-active substances which are endogenous to the skin, skin fats are also dissolved and washed out to a certain extent. After initial swelling, this causes the skin subsequently to dry out, a process which may be further substantially intensified by detersive additives.

In healthy skin, these processes are generally of no consequence, since the protective mechanisms of the skin are easily able to compensate for such slight disturbances to the upper skin layers. However, even in the case of non-pathological deviations from the normal state, as a result, for example, of environmentally induced wear damage or irritation, photodamage, aging skin, and so on, the protective mechanism at the skin's surface is impaired.

In the case of aged skin, for example, regenerative renewal takes place at a slower rate, and the water-binding capacity of the horny layer, in particular, suffers a decrease. The skin therefore becomes inflexible, dry, and chapped ("physiologically" dry skin). Barrier damage is the result. The skin becomes susceptible to adverse environmental influences such as the invasion of microorganisms, toxins, and allergens. As a consequence, toxic or allergic skin reactions may even occur.

In the case of pathologically dry and sensitive skin, barrier damage is present a priori. Epidermal intercellular lipids become defective or are formed in inadequate amounts or compositions. The consequence is an increased permeability of the horny layer and inadequate protection of the skin against loss of hygroscopic substances and water.

The barrier effect of the skin can be quantified via the determination of the transepidermal water loss (TEWL). This is the evaporation of water from inside the body, without taking account the loss of water during perspiration. Determining the TEWL value has proven extraordinarily informative and can be used to diagnose chapped or cracked skin, to determine the compatibility of surfactants with different kinds of chemical compositions, and more besides.

For the beauty and well-cared-for appearance of the skin, the proportion of water in the topmost layer of the skin is of the utmost importance. Within a limited extent it can be favorably influenced by the introduction of moisture regulators.

Anionic surfactants, which are generally constituents of cleansing preparations, are able lastingly to increase the pH in the horny layer, which severely hinders regenerative processes that serve to restore and renew the barrier function of the skin. In this case, a new, frequently very adverse state of equilibrium is established in the horny layer between regeneration and the loss of essential substances as a result of regular extraction; this equilibrium state has a decisive adverse effect on the external appearance of the skin and on the physiological functioning of the horny layer.

Cosmetic skin care means primarily that the natural function of the skin as a barrier against environmental influences, e.g., dirt, chemicals, microorganisms, and against the loss of substances endogenous to the body, e.g., water, natural fats, electrolytes, is strengthened or restored.

If this function is disrupted, there may be increased absorption of toxic or allergenic substances or infestation by microorganisms and, as a consequence, toxic or allergic skin reactions.

A further aim of skin care is to compensate the loss of fat and water as a result of daily washing. This is particularly important if the natural regeneration capacity is insufficient. Moreover, skin care products ought to protect against environmental effects, especially against sun and wind, and ought to delay skin aging.

Chronological skin aging is caused, for example, by endogenous, genetically determined factors. As a result of aging, within the epidermis and dermis, the following structural damage and functional disorders, for example, occur, which may also come under the term "senile xerosis":

a) dryness, roughness, and formation of dryness wrinkles
b) itching, and
c reduced fat restoration by sebaceous glands, e.g., after washing.

Exogenous factors, such as UV light and chemical noxae, may have a cumulative effect. Within the epidermis and dermis, in particular as a result of exogenous factors, the following structural damage and functional disorders, for example, occur in the skin:

d) increased susceptibility to mechanical stress, e.g., chapping.

Products for the care of sensitive, itchy and/or dry skin or products for the treatment of or prophylaxis of DNS damage are known per se. Their efficacy, though, is limited.

The present invention relates in particular also to cosmetic preparations that provide additional, effective protection against damaging oxidation processes in the skin, but also for the additional protection of cosmetic preparations themselves and/or for the additional protection of the constituents of cosmetic preparations against harmful oxidation processes.

It would be advantageous to be able to provide cosmetic and dermatological preparations based on a gel matrix, in particular including suitable active substances, which counter the above-described unwanted skin phenomena such as the dryness, roughness, chapping and reduced fat restoration of the skin,
the after-effects of exogenous exposures such as UV light and shaving, especially sunburn and shaving burn,
other irritant and inflammatory skin reactions, including itchy skin,
hair growth as a cosmetic desire, such as in the case of woman's beard, for example,
aging skin phenomena such as lack of elasticity, increasing wrinkliness and age spots and to strengthen the physiology of the skin with regard to
the barrier properties,
the maintenance of skin homeostasis,
the growth of the hair as a cosmetic desire and also to enable a cosmetically desired
modulation of the pigmentation of skin and hair.

With topical application of the cosmetic or dermatological preparations of the invention, comprising an effective amount of active substances used, it is surprisingly possible to achieve effective treatment, but also prophylaxis, in the case of reduced skin hydration or reduced moisture content of the skin
aging skin wrinkles
photo-aged skin
greasy and unclean skin
reduced skin elasticity
age spots and other abnormal pigmentations of the skin, e.g., melasma,
after-reactions of the skin to UV light (sunburn)
after-reactions of the skin to shaving (shaving burn)
dysfunction of metabolic homeostasis of the skin
reduced cell-cell communication
reduced DNA synthesis and/or reduced DNA repair
activation of metalloproteinases and/or proteases
activation of cyclooxygenases and lipoxygenases of the skin
alterations to normal hyaluronic acid and glucosaminoglycan homeostasis
deviations from the normal post-translational modifications of connective-tissue proteins, glycosaminoglycans and other structural constituents
disruptions to the ceramide, lipid and energy metabolism of the skin
disruptions to melanin metabolism and the melanosoma processing of the skin
deficient, sensitive or hypoactive skin conditions or deficient, sensitive or hypoactive conditions of skin appendages
changes in transepidermal water loss
changes in the amount of natural moisturizing factor
changes in normal lipid peroxidation
inflammatory phenomena and/or itching
formation of flakes in the hair region
reduced and also unwanted hair growth
disruptions to the barrier function.

Additionally it has been found that when a preparation according to the invention is employed it may be possible to increase the general sensation of freshness of the skin.

The mechanism of action of patches or cosmetic matrices for administering cosmetic substances into and onto the skin is subject to a functional principle similar to that of transdermal therapeutic systems (TTS). The terms patches, cosmetic/dermatological matrices and cosmetic/dermatological pads are sometimes used synonymously below.

Transdermal therapeutic systems for delivering active substances into and/or through the skin have been known for a long time and constitute patch-like systems which in particular are doped with drugs.

The topical administration of active cosmetic and dermatological substances via patch systems or cosmetic matrices offers two main advantages:

First, this administration form produces first-order release kinetics of the active substance, thereby allowing a constant level of active substance to be maintained in the skin over a very long period of time.

Secondly, an additional intensive care of the skin can be brought about via appropriate systems.

The time-dependent release of the active cosmetic substance from a TTS takes place in dependence on its TTS/skin partition coefficient and its diffusion in the region of the TTS and of the skin.

Both factors are determined by the composition of the matrix, thereby allowing the amount released per unit time and the duration of activity to be influenced directly. Normally hydrocolloids, solubilizers and enhancers are used for this purpose, allowing improved solubility and diffusion and also a more rapid passage of the substance from TTS into the skin.

Ideally, first-order release kinetics are achieved, allowing the release of equal quantities per unit time.

One embodiment of such transdermal systems which has been well described in the technical literature is that of matrix systems or monolithic systems in which the active cosmetic substance is incorporated directly into the pressure-sensitive adhesive. In the ready-to-apply product a pressure-sensitive adhesive matrix of this kind, comprising active substance, is equipped on one side with a backing, which is occlusive for the active substance, while on the opposite side there is a backing film equipped with a release layer, which is removed prior to application to the skin (kleben&dichten, No. 42, 1992, pp. 26 to 30).

The aforementioned properties of a TTS avoid the need for frequently repeated administration and avoid burdening the skin with high concentrations of active substances, and so reduce irritation to the skin, which is unavoidable in the event of repeated administration of liquid and semisolid administration forms.

In summary, the advantages of the TTS lie in a distinctly improved compliance on the part of users, which is attributable to the simple and rapid administration and to the long-lasting efficacy of transdermal therapeutic systems.

One basic requirement of a TTS is effective adhesion to skin, which must be maintained over the entire period of the intended dosing of active substance, and another is the ability for the TTS to be removed without residue. Painful redetachment of the active substance patch after a prolonged period of wear is a frequent observation. As well as adhesives which are coated in solution onto the backing, the adhesives used also include solvent-free systems, such as hot-melt adhesives. A feature of these adhesives is that in the course of their coating it is possible to forego the use of organic solvent and dispersion medium. Hot-melt adhesives are converted to a liquid form by heating and are applied thus as a melt to the respective patch backing. As well as technical aspects, such as solvent processing, plant design with anti-explosion measures, and environmental protection strictures, medical reasons as well play a part in the choice of solvent-free adhesives. Transdermal therapeutic systems are generally applied to healthy, intact skin.

Self-adhesive matrix systems for administering active cosmetic substances are among traditional applications in Asia, particularly in Japan, and are defined in the Japanese pharmacopoeia under the terms "cataplasm". Cataplasms, accordingly, are commonly prepared by mixing glycerin, water or other suitable liquids with finely pulverized active substances, with the addition of essential oils.

Glycerin functions here as a humectant, in order to prevent the cataplasms from drying out prematurely in use.

Whereas in the traditional Asian preparations natural thickeners such as alumina, etc., are employed, recent decades have seen the use, more and more, of modern synthetic raw materials, such as polyacrylic acid as a gel former, for example, for their production. This allows the cataplasms, which are commonly pasty, to be produced as hydrogel matrices having improved attractiveness and user-friendliness.

EP 1 136 057 describes an aqueous gel system for cosmetic use without backing or liner, with a light transmittance of min. 70%.

EP 0 507 160 describes cataplasms containing lidocaine.

A disadvantage of the cataplasms described is that the production of the base matrices requires many different individual components such as gel formers, thickeners, plasticizers, humectants, stabilizers, emulsifiers, pH regulators, antioxidants, etc., and possibly also solubilizers and penetration enhancers in the case of active substance cataplasms. Since the adhesive performance and consistency of such a matrix is a function of the interaction of all of the individual components, targeted product development/optimization with regard to these fundamental product requirements is, correspondingly, time-consuming and arduous.

The production of polymer matrices, especially gel matrices, from polyacrylates has likewise been known for many years and is described for example in EP 0 507 160, JP 11-228340 and JP 04178323. Gel matrices are used, among other things, as an adhesive base and as an active substance reservoir in transdermal systems. Such systems have an adequate bond strength, especially to moist skin (buccal patches), but because of inadequate cohesiveness cannot be removed again completely when required.

In order to form a gel with a defined structure it is necessary for polyacrylic acid to be cross-linked. The nature of the cross-linker makes a critical contribution to the structure of the resultant gel. The customary cross-linking agents may be metal ions (e.g.: $Al^{3+}$ ions), or organic compounds. Cross-linking with aluminum salts proceeds via the coordination of the oxygen functions of the polyacrylic acid to the $Al^{3+}$ ions. A very close-meshed gel with high viscosity is formed, the viscosity of the gel being controllable only via the amount of cross-linker (Handbook of Pressure Sensitive Technology, page 458 ff, 1999).

JP 11-228340 discloses polyacrylic acid-based gels which utilize $Al^{+3}$ compounds as cross-linkers. The use of the mandatory aluminum compound as a cross-linking agent is limited, since otherwise the physical properties of the gel are impaired. If the proportion of aluminum cross-linker is too high the gel becomes too hard.

Known from the literature are further examples of cross-linking with polyvalent metal ions, e.g., U.S. Pat. No. 3,900,610 (zinc salts), U.S. Pat. No. 3,770,780 or U.S. Pat. No. 3,790,533 (titanium compounds). Ionic cross-linking with metal ions leads to hard, viscous polymer gels with low tack (Handbook of Pressure Sensitive Adhesive Technology, page 458 ff, 1999).

EP 303445 discloses a patch with a monolithic gel matrix based on water-soluble polymers. Mandatory constituents are clebopride or a pharmaceutically acceptable salt thereof as active substance, water, water absorbers, and water-soluble polymers. As water-soluble polymers the skilled worker is able to select from a range of known polymers such as polyvinyl alcohol, gelatin, polyacrylic acid, sodium polyacrylates, methylcellulose, carboxymethylcellulose, polyvinylpyrrolidone, rubber and other cross-linkable polymers and also mixtures thereof.

EP 976382 describes a patch comprising a matrix composed of a system which is hydrophilically gelling in aqueous phase and which is formed from gelan gum and at least one further hydrocolloid. Gelan gum is claimed mandatorily. Gelan gum is understood by the skilled worker, as defined by technical dictionaries, to comprise hydrocolloids obtained from the following marine plants: Agardhiella tenera, Furcellaria fastigiata, Hypnea cervicornis, musciformis, spicifera, Suhria vitata. The term does not comprise sea algae extracts. Nor is there any mention of the essential aspects of self-adhesive properties, the adjustability of bond strength and elasticity of the resultant matrices.

A further problem associated with the cross-linking of polyacrylic acid to form a self-adhesive matrix or gel is that a matrix once produced, having defined physical properties, viscosity, tack, etc., must have the same defined properties in a later production operation. This reproducibility is difficult if not impossible to realize with the cross-linking technologies that are presently known.

A further problem apparent in connection with cosmetic skin treatment is that unwanted skin phenomena cannot be given optimum treatment by the topical application of active substances in the form of emulsion formulations and the like. Particularly in the case of skin phenomena which are relatively difficult to treat, such as wrinkles, loss of skin elasticity, and age spots, and also irritative skin phenomena such as sunburn and shaving burn, etc., there is a lack of a cosmetic application system which offers intensive provision of the active substance in conjunction with beneficial effects on the skin in order to influence the skin condition positively.

It would therefore be desirable to develop a simple polymer matrix system for cataplasms/hydrogels which, with a few ingredients, allows matrices of defined consistency and bond strength to be produced in a controlled fashion.

It would further be advantageous to have available a polymer matrix in which water-soluble or hydrophobic active substances can be incorporated and can be delivered to the skin in a controlled fashion.

It would further be desirable to be able to provide patches or cosmetic matrices which comprise aforementioned polymer matrices and can be used as TTS, pads or patches.

It would further be desirable to be able to provide a gel matrix suitable as a cosmetic application form for the treatment and also for the prophylaxis of unwanted skin phenomena, and to remedy the disadvantages of the prior art. In this context the aim in particular is to take into account the skin care and moisturizing aspect.

SUMMARY OF THE INVENTION

The present invention provides a self-adhesive polymer matrix which comprises (a) at least one polymer which forms a gel in water, (b) water, (c) a sea algae extract, and (d) at least one alcohol which is a monohydric or polyhydric alcohol.

In one aspect of the polymer matrix, component (a) may comprise a polyacrylic acid polymer. By way of non-limiting example, the polyacrylic acid polymer may comprise an acrylate-alkyl acrylate copolymer with the structure:

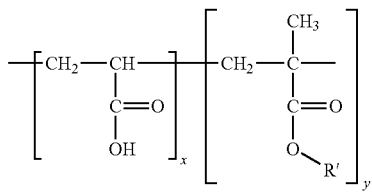

where R' is an alkyl radical and x and y indicate the stoichiometric fraction of the respective comonomers and/or may comprise a copolymer of a $C_{10-30}$ alkyl acrylate and acrylic acid, methacrylic acid and/or esters thereof, which copolymer is crosslinked with an allyl ether of sucrose or with an allyl ether of pentaerythritol.

In another aspect, the polymer matrix may comprise from 2% to 55% by weight of component (a), based on the total weight of the matrix, e.g., at least 5% by weight and/or not more than 30% by weight of component (a).

In yet another aspect of the polymer matrix of the present invention, component (c) may comprise agar-agar and/or carrageenan. In another aspect, component (c) may be present in a concentration of 0.1% to 15% by weight, based on the total weight of the matrix, e.g., in a concentration of at least about 0.5% by weight and/or not more than 5% by weight.

In a still further aspect of the polymer matrix of the present invention, component (d) may comprise one or more of glycerin, propanediol and sorbitol, preferably glycerin. In another aspect, component (d) may be present in a concentration of from 1% to 85% by weight, based on the total weight of the matrix, e.g., in a concentration of at least 5% by weight and/or not more than 45% by weight.

In another aspect of the polymer matrix of the present invention, the polymer matrix of the present invention may further comprise (e) at least one active substance, for example, at least one dermatological or cosmetic substance. By way of non-limiting example, component (e) may comprise one or more of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts such as soya and clover extracts, ubiquinone Q10, sericosides, tyrosine sulfate, jojoba oil and aloe vera, and/or component (e) may comprise a disinfectant and/or an antiseptic.

In yet another aspect, the polymer matrix of the present invention may further comprise up to 35% by weight, e.g., up to 15% by weight of component (e), based on the total weight of the matrix. For example, component (e) may be present in a concentration of at least 0.02% by weight and/or not more than 2% by weight.

The present invention also provides a self-adhesive polymer matrix which comprises from 2% to 55% by weight of (a) at least one polymer which forms a gel in water, (b) water, from 0.1% to 15% by weight of (c) a sea algae extract, and from 1% to 85% by weight of (d) at least one monohydric or polyhydric alcohol, each based on the total weight of the matrix.

In one aspect, the polymer matrix may comprise from 5% to 30% by weight of component (a), from 0.5% to 5% by weight of component (c), and from 5% to 45% by weight of component (d) and/or component (a) may comprise at least one polyacrylic acid polymer, component (c) may comprise agar-agar and/or carrageenan, preferably agar-agar, and component (d) may comprise one or more of glycerin, propanediol and sorbitol, preferably glycerin.

In another aspect of the polymer matrix, the matrix may further comprise up to 35% by weight of (e) at least one dermatological or cosmetic active substance, based on the total weight of the matrix. By way of non-limiting example, component (e) may comprise one or more of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera. In another aspect, component (e) may comprise a disinfectant and/or an antiseptic.

The present invention also provides a self-adhesive polymer matrix which comprises from 5% to 30% by weight of (a) at least one polymer which forms a gel in water and comprises at least one polyacrylic acid polymer, (b) water, from 0.5% to 5% by weight of (c) a sea algae extract which comprises agar-agar and/or carrageenan, from 5% to 45% by weight of (d) one or more monohydric or polyhydric alcohols which comprise glycerol, and from 0.02% to 2% by weight of (e) at least one dermatological or cosmetic active substance, each based on the total weight of the matrix.

In one aspect, component (e) may comprise one or more of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera, and/or component (e) may comprise at least one substance that is a disinfectant or an antiseptic.

The present invention also provides a patch, a cosmetic or dermatological matrix or a pad that comprises a polymer matrix as set forth above, including the various aspects thereof.

The present invention also provides a two-dimensional product that comprises the polymer matrix set forth above, including the various aspects thereof, and has a total area of from 0.2 to 1000 cm$^2$, as well as a two-dimensional or three-dimensional product which comprises from 0.1 to 1,000 g, e.g., 500 g, of the polymer matrix.

The present invention also provides a skin care method which comprises the application of a product that comprises the polymer matrix set forth above and comprises a skin care agent to the skin.

The present invention also provides a method of administering an active substance, which method comprises the application of the active substance in the polymer matrix set forth above to a body surface. For example, the polymer matrix may be applied topically or buccally and/or the polymer matrix may be a component of a transdermal therapeutic system, e.g., a monolithic transdermal therapeutic system.

The present invention also provides a method for the prophylaxis or treatment of skin aging phenomena such as, e.g., wrinkles, which method comprises the application of a product that comprises the polymer matrix set forth above to the skin.

The present invention also provides a method for the prophylaxis or treatment of skin pigmentation disorders such as, e.g. age spots, which method comprises the application of a product that comprises the polymer matrix set forth above to the skin.

The present invention also provides a method for the prophylaxis or treatment of inflammatory or irritative skin phenomena such as, e.g., shaving burn and/or sunburn, which method comprises the application of a product that comprises the polymer matrix set forth above to the skin.

Surprisingly it has emerged in particular that the cosmetic matrix described, even without an active substance, per se, has skin care, moisturizing, and cooling properties and can therefore be used, even without the introduction of active substance, in order to remedy the disadvantages of the prior art;

a form of application which is very practicable and pleasant for the user is presented, since, through the use of a suitable fleece material, in contrast to many cosmetic towels, which hence are impregnated, the surface is dry and appears with a pleasantly silky feel; and as a result of the introduction of one or more active substances, it is possible to positively counter the unwanted skin conditions, or to serve as prophylaxis.

The present invention relates to a cosmetic or dermatological formulation which is suitable in particular for supplying active cosmetic or dermatological substances to the skin in a particularly effective way and, moreover, for doing so in a form which is particularly cosmetic and pleasant for the user.

The matrix is composed of a polymer which forms a gel (gels) in water, preferably a polyacrylic acid gel, as a bond-strength-determining component. The sea algae extract is preferably agar-agar. As alcohol use is made in particular of monohydric or polyhydric alcohols, preferably glycerin, which act as consistency factors. Despite the fact that the individual components are known for use for producing cataplasms or hydrogels, it was not hitherto known to employ agar-agar in conjunction with glycerin, for example, specifically as consistency factors for polyacrylic acid matrices.

An increase in the fraction of sea algae extract in polymer matrices, such as cataplasms/hydrogels, increases the strength of the matrices. However, it also increases the stiffness and reduces the tack. This disadvantage can be compensated by adding alcohol, especially glycerin. It is therefore possible to set a desired elasticity in the resultant polymer matrix in conjunction with a constant fraction of sea algae extract.

Accordingly, a synergistic combination of sea algae extract and monohydric or polyhydric alcohols, preferably glycerin, ensures a desired elasticity in the gel matrices.

The basis for its use as a consistency factor is that sea algae extract, in contrast to, in particular, the widespread gelatin and other consistency factors, does not induce gelling in conjunction with alcohols, such as glycerin or propanediol, for example. Since monohydric or polyhydric alcohols according to the invention, such as glycerin or propanediol, are distributed homogeneously in water but do not form gels with the sea algae extract, alcohols of this kind hence act as an elasticity factor for the matrices.

A sea algae extract whose use is preferred, besides agar-agar, is carrageenan. Carrageenan is a hydrophilic polysaccharide of high molecular weight which is obtained from various red algae, principally Chondrus crispus, by hot-water extraction, subsequent freezing and following cleaning. The structure of carrageenan is composed primarily of repeating units of galactose and 3,6-anhydrogalactose, both in sulfated and unsulfated form. The principal distinction between kappa, iota and lambda carrageenan is the number and position of the ester sulfate groups on the repeating galactose units.

Gelling of carrageenan is possible only in the presence of cations. Preference in accordance with the invention is given to kappa and iota carrageenan, which form gels in the presence of calcium ions (kappa and iota), potassium ions and ammonium ions (kappa only). Particularly advantageous is the use of corresponding cation hydroxides, since the polyacrylic acid likewise used for producing gel matrix systems of the invention must be neutralized in order to form stable gels.

Carrageenan is available commercially from, for example, Lehmann & Voss & Co. under the names Gelcarin, Viscarin and Seaspen.

Sea algae extract, such as with particular preference in accordance with the invention agar-agar, is a hydrophilic colloid of polysaccharide structure composed of the gelling agarose and the non-gelling agaropectin, which is obtained from various marine algae of the Rhodophyceae class by hot-water extraction, subsequent freezing and following cleaning. Agar-agar is available commercially from, for example, Riedel de Haen A G.

The extract, especially agar-agar or carrageenan, is used preferably in an amount of 0.1%-15% by weight, more preferably between 0.5%-5% by weight. All percentages here are based on weight fractions of the polymer matrix, unless indicated to the contrary.

Monohydric or polyhydric alcohols such as, for example, glycerin (1,2,3-propanetriol) are pharmaceutical industrial auxiliaries that enjoy widespread use, inter alia, as solubilizers or humectants.

Monohydric or polyhydric alcohols, such as glycerin, for example, are used in accordance with the present invention with preference in an amount of 1%-85% by weight, more preferably between 5%-45% by weight.

The fraction of polymer which forms a gel in water, such as polyacrylic acid gel, for example, in the matrix governs the adhesion. In contrast to agar-agar, polyacrylic acid forms gels both with water and with alcohols, so that the adhesion set by the fraction of polyacrylic acid remains constant independently of the particular alcohol fraction.

Polyacrylates that are advantageous in accordance with the invention are acrylate-alkyl acrylate copolymers, particularly those chosen from the group of what are called carbomers or carbopols (Carbopol® is a registered trademark of the B. F. Goodrich Company). In particular the acrylate-alkyl acrylate copolymer or copolymers that is or are advantageous in accordance with the invention is or are characterized by the following structure:

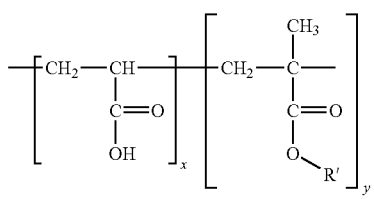

In this structure R' is an alkyl radical, in particular a long-chain alkyl radical, and x and y are numbers which indicate the respective stoichiometric fraction of the respective comonomers.

Acrylate copolymers and/or acrylate-alkyl acrylate copolymers that are particularly preferred in accordance with the invention are those available under the commercial designations Carbopol® 1382, Carbopol® 981 and Carbopol® 5984 from the B. F Goodrich Company, preferably polyacrylates from the group of the Carbopols of types 980, 981, 1382, 2984 and 5984, and more preferably Carbomer 2001.

Advantageous further are copolymers of $C_{10-30}$ alkyl acrylates and one or more monomers of acrylic acid, of methacrylic acid or of esters thereof, which are crosslinked with an allyl ether of sucrose or with an allyl ether of pentaerythritol.

The polymer which forms a gel in water, especially polyacrylic acid and/or copolymers thereof, is used preferably in an amount of 2%-55% by weight, or preferably between 5%-30% by weight.

The polymer matrices are prepared without the use of organic solvents, preferably at 40-95° C., in standard commercial mixers/compounders or, continuously, in suitable extruders.

A further suitable polymer which forms a gel in water is inter alia baobab flour.

In this way it is possible, using only water, polymer which gels in water, sea algae extract, and monohydric or polyhydric alcohol as starting materials, to produce, in a targeted fashion, soft, smooth, self-adhesive hydrogel matrices as a basis for production and use as patches, TTS, cataplasms or cosmetic pad/matrices.

In order to produce particular performance properties it is possible for the polymer matrices to be admixed with appropriate plasticizers, solubilizers, penetration enhancers, neutralizing agents such as tromethamol (2-amino-2-(hydroxymethyl)-1,3-propanediol), triethanolamine (2,2',2"-nitrilotriethanol) or NaOH, for example, fillers and/or other known additives, although it is not mandatory to add them.

In one embodiment which is particularly preferred in accordance with the invention the polymer matrix or gel matrix contains active dermatological or cosmetic substances for controlled local and/or systemic delivery onto/into the skin, in amounts of 0-35% by weight, preferably 0-15% by weight.

The gel matrix can thus be doped with hydrophilic active substances, or else, in the presence of an appropriate solubilizer, with hydrophobic active substances, for the cosmetic treatment of unwanted skin phenomena. In the case of incorporation of hydrophobic active substances it may be of benefit to use cyclodextrins for encapsulation.

Cyclodextrins (cycloamyloses, cycloglucans) are known per se in cosmetic and pharmaceutical preparations.

Improving the solubility of substances of sparing solubility, in the presence of cyclodextrins in an aqueous medium, has been described for individual substances. Advantageous may be both the inclusion compounds of a substance, also called the guest, with a cyclodextrin species—in this context both 1:1 or 1:2 complexes and complexes with other molar ratios (guest:cyclodextrin) are possible—and the physical mixtures thereof.

The cyclodextrins are cyclic oligosaccharides composed of α-1,4-linked glucose units. In general, six to eight glucose units (α-, β-, or γ-cyclodextrin) are joined to one another. Cyclodextrins are obtained when starch is acted on by *Bacillus macerans*. They possess a hydrophobic interior and a hydrophilic exterior. By virtue of their structure, cyclodextrins and their derivatives are able to form inclusion complexes. They are suitable for the "molecular encapsulation" of active substances (e.g., as a protective envelope around sensitive molecules in cosmetic and pharmaceutical formulations).

These applications are also described in a series of patents, e.g., WO 98/55148, EP 0 579 435, EP 0 392 608. In these publications, however, usually only one active substance is complexed by the cyclodextrin (derivative). While multi-component inclusion complexes are described in EP 0756 493, when looked at more closely the latter relates to a salt and not to a two-component mixture of acid and base.

In the following the phrase "cyclodextrin and/or a derivative thereof" refers both to cyclodextrins having different numbers of glucose units in the ring molecule, and to derivatives of these compounds.

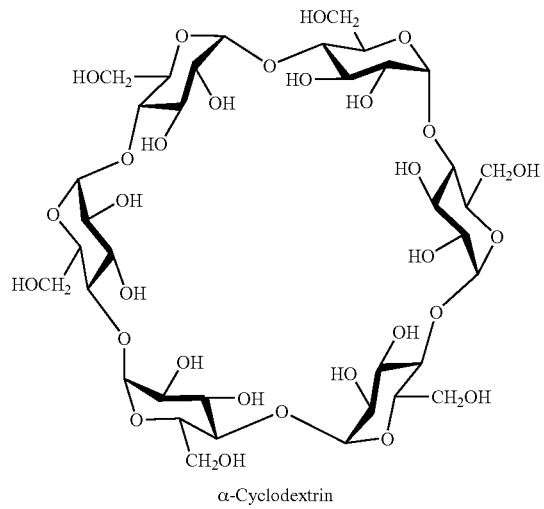

α-Cyclodextrin

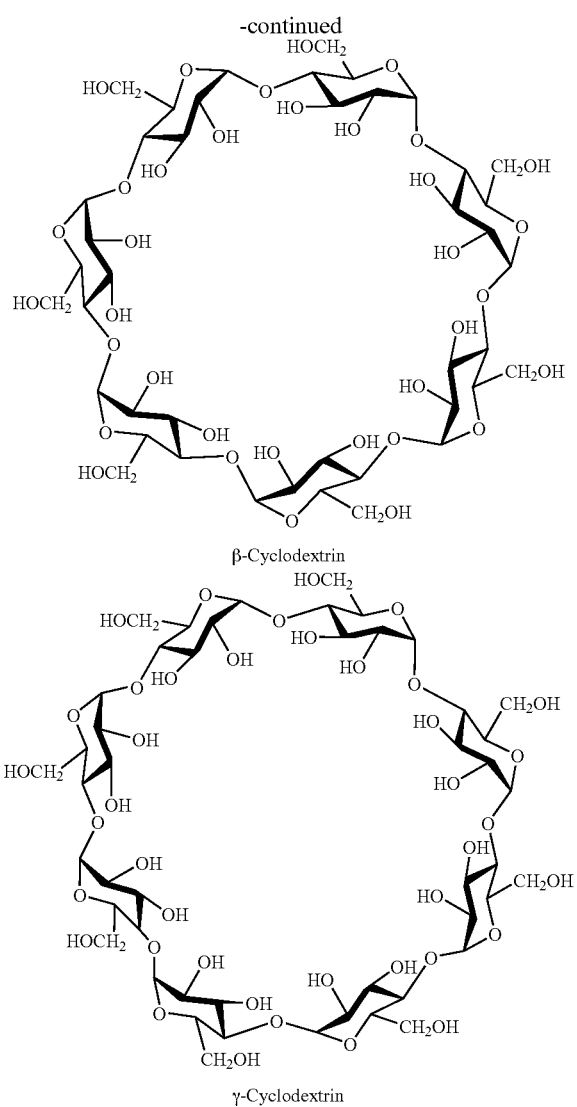

β-Cyclodextrin

γ-Cyclodextrin

In accordance with the invention the cyclodextrin or cyclodextrins is or are used preferably in cosmetic or dermatological compositions in a concentration of 0.0005% to 20.0% by weight, in particular 0.01% to 10% by weight, and more preferably in a concentration of 0.1% to 5.0% by weight.

It is advantageous in accordance with the invention to use native cyclodextrins or cyclodextrins with polar and/or apolar substitution. These include preferably, but not exclusively, methyl-, especially random-methyl-β-cyclodextrin, ethyl- and also hydroxypropyl-cyclodextrins, such as HP-β-cyclodextrin or HP-γ-cyclodextrin, for example.

The cyclodextrin species that are particularly preferred in accordance with the invention are γ-cyclodextrin and also hydroxypropyl-β-cyclodextrin.

Further prior art is contained in the following publications:

K. Uekama et al., Chemical Reviews, 1998, 98, 2045-2076, "Cyclodextrin drug carrier systems"

T. Loftsson, Int. J. Dermatology, 1998, 37, 241-246, "Cyclodextrins: new drug delivery systems in dermatology".

J. Zatz et al. Cosmetics & Toiletries, 1997, 112, July, p. 39 ff, "Applications of cyclodextrins in skin products".

U. Citernesi, Cosmetics & Toiletries, 1995, 110, March, p. 53 ff, Cyclodextrins in functional dermocosmetics.

The cyclodextrins and/or cyclodextrin-guest inclusion complexes and/or the cyclodextrin substance mixtures used in accordance with the present invention can be incorporated into the polymer matrix without difficulties.

Since the matrix of the invention is a water-containing application form, a cooling effect is obtained in addition, this effect already per se being cosmetically pleasant and contributing to well-being. This positive effect can be intensified by the addition of further care constituents. Besides glycerin it is possible in particular to add serinol (3-amino-1,2-propanediol) and/or isoserinol (2-amino-1,3-propanediol) and also urea and PCA (pyrrolidone carboxylic acid) as moisturizers. It is of course also possible to add further substances for this purpose.

As particularly suitable active substances in the sense of the invention it is possible for active substances below, either individually or else in combination, to be added to the stated cosmetic matrices/pads.

In the context of the present invention it has surprisingly emerged that the formulations of the invention are also especially suitable for the use of active substances which have a positive influence on skin condition. Thus it has been found that active substances for positively influencing aging skin, which reduce the formation of wrinkles or even lessen existing wrinkles. Particularly preferred active substances are therefore considered to be bioquinones, especially ubiquinone, Q10, creatine, creatinine, carnitine, acetylcarnitine, biotin, isoflavone and isoflavonoids, genistein, arctiine, cardiolipine, lipoic acid, anti-freezing proteins, hop extracts and hop-malt extracts, and/or substances which promote restructuring of the connective tissue, isoflavonoids and isoflavonoid-containing plant extracts such as soya extracts and clover extracts, for example, which can be used very effectively in the matrices of the invention.

Also it has been found that the matrix is particularly suitable for using active substances for assisting skin functions in the case of dry skin, such as vitamin C, biotin, carnitine, creatine, creatinine, propionic acid, glycerin, green tea extracts, eucalyptus oil, urea and mineral salts such as NaCl, marine minerals and also osmolytes such as, for example, taurine, inositol, betaine, and quaternary ammonium compounds.

Similarly, the incorporation of active substances for alleviating or positively influencing irritative skin conditions proved advantageous, whether for sensitive skin in general or for skin irritated by noxae (UV light, chemicals). Active substances to be mentioned here are substances such as sericosides, various extracts of liquorice, licochalcone A, silymarin and/or silyphos, dexpanthenol, ethanol, inhibitors of prostaglandin metabolism, particularly of cyclooxygenase, and of leukotriene metabolism, particularly of 5-lipoxygenase, but also of the 5-lipoxygenase inhibitor protein, FLAP.

The incorporation of pigmentation modulators also proved advantageous. Active substances to be mentioned here are substances which reduce the pigmentation of the skin and so lead to a cosmetically desired lightening of the skin and/or which reduce the incidence of age spots and/or lighten existing age spots, such as tyrosine sulfate, dioic acid (8-hexadecene-1,16-dicarboxylic acid), lipoic acid and liponamide, various extracts of liquorice, kojic acid, hydroquinone, arbutin, fruit acids, especially alpha-hydroxy acids (AHAs), bearberry (Uvae ursi), ursolic acid, ascorbic acid, green tea extracts, aminoguanidine and/or pyridoxamine.

In the same way the matrices of the invention proved to be an outstanding basis for active substances which bring about increased/more rapid tanning of the skin (advanced glycation end products (AGE)), lipofuscins, nucleic acid oligonucleotides, purines and pyrimidines, NO-releasing substances, whether with or without the influence of UV light.

The polymer matrix will contain the active substance or substances in amounts of 0-35% by weight, preferably 0-15% by weight, very preferably 0.02%-2%.

For the prophylaxis of oxidative and degenerative damage and in particular for the treatment of such damage it has surprisingly been found advantageous to add antioxidants to the cosmetic matrices/pads. The antioxidants are advantageously selected from amino acids, e.g. glycine, lysine, arginine, cysteine, histidine, tyrosine, tryptophan, and their derivatives (as salt, ester, ether, sugar, nucleotide, nucleoside, peptide and/or lipid compound), imidazoles, e.g. urocanic acid, and their derivatives as salt, ester, ether, sugar, nucleotide, nucleoside, peptide and/or lipid compound, peptides such as D,L-carnosine, D-carnosine, L-carnosine, anserine and derivatives thereof, e.g., as salt, ester, ether, sugar, thiol, nucleotide, nucleoside, peptide and/or lipid compound, carotenoids, carotenes, e.g., α-carotene, β-carotene, ψ-lycopene, phytoene, and derivatives thereof, e.g. as salt, ester, ether, sugar, nucleotide, nucleoside, peptide and/or lipid compound, chlorogenic acid and derivatives thereof, as salt, ester, ether, sugar, thiol, nucleotide, nucleoside, peptide and/or lipid compound, aurothioglucose, propylthiouracil and other thiols, e.g. thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters, and also salts thereof, dilauryl thiodipropionate, distearyl thiodipropionate, thiodipropionic acid and derivatives thereof, as salt, ester, ether, sugar, thiol, nucleotide, nucleoside, peptide and/or lipid compound, and also sulfoximine compounds, e.g. homocysteine sulfoximine, buthionine sulfones, penta-, hexa-, heptathionine sulfoximine, in very low tolerated doses, e.g., pmol to μmol/kg. Additionally (metal) chelating agents, e.g., apoferritin, desferral, lactoferrin, α-hydroxy fatty acids, palmitic acid, phytic acid, and derivatives thereof, as salt, ester, ether, sugar, thiol, nucleotide, nucleoside, peptide and/or lipid compound, α-hydroxy acids, e.g., citric acid, lactic acid, malic acid, humic acid, bile acid, bile extracts, bilirubin, biliverdin, melanin, EDTA, EGTA and derivatives thereof, unsaturated fatty acids and their derivatives, e.g., γ-linolenic acid, linoleic acid, oleic acid, folic acid and derivatives thereof, furfurylidenesorbitol and its derivatives, ubiquinone, ubiquinol, plastoquinone and derivatives thereof, as salt, ester, ether, sugar, thiol, nucleotide, nucleoside, peptide and lipid compound, vitamin C and derivatives, e.g., ascorbyl palmitate, Mg-ascorbyl phosphate, ascorbyl acetate, tocopherols and derivatives, e.g. vitamin E acetate, Trolox®, and also phenolic compounds and plant extracts comprising them, such as flavonoids, for example, e.g., glycosylrutin, ferulic acid, caffeic acid, furfurylideneglucitol, butylated hydroxytoluene, butylhydroxyanisole, nordihydroguaiacic acid, nordihydroguaiaretic acid, trihydroxybutyrophenone and derivatives thereof, as salt, ester, ether, sugar, nucleotide, nucleoside, peptide and lipid compound, uric acid and derivatives thereof, mannose and derivatives thereof, as salt, ester, ether, sugar, thiol, nucleotide, nucleoside, peptide and lipid compound, zinc and its derivatives, e.g. ZnO, ZnSO$_4$, selenium and its derivatives, e.g. selenium methionine, ebselen, stilbenes and derivatives thereof, e.g., stilbene oxide, trans-stilbene oxide, and the derivatives that are suitable in accordance with the invention, as salt, ester, ether, sugar, thiol, nucleotide, nucleoside, peptide and/or lipid compound, of these stated active substances.

The polymer matrix will contain the antioxidant or antioxidants in amounts of 0-35% by weight, preferably 0-15% by weight, very preferably 0.02%-2%.

Further examples of active substances which can be used include essential oils. By essential oils are meant plant-derived concentrates which as natural raw materials are used primarily in the fragrance and foodstuffs industries and are composed more or less of volatile compounds. Examples that may be mentioned of these compounds include 1,8-cineol, limonene, menthol, borneol and camphor. The term "essential oils" is often used for the volatile constituents still present in the plants. In their true sense, however, essential oils are understood to be mixtures of volatile compounds prepared by steam distillation from plant raw materials.

Essential oils are composed exclusively of volatile components, whose boiling points are in general between 150 and 300° C. They include predominantly hydrocarbons or monofunctional compounds such as aldehydes, alcohols, esters, ethers and ketones. Parent compounds are mono- and sesquiterpenes, phenylpropane derivatives and longer-chain aliphatic compounds.

In some essential oils, one constituent is dominant (for example, eugenol in clove oil, at more than 85%), while other essential oils constitute complex mixtures of the individual constituents. Often the organoleptic properties are determined not by the main components but by subsidiary or trace constituents, such as, for example, by the 1,3,5-undecatrienes and pyrazines in galbanum oil. The number of identified components in many of the commercially significant essential oils is up into the hundreds. Very many constituents are chiral, with very often one enantiomer being predominant or being present exclusively, such as (−)-menthol in peppermint oil or (−)-linalyl acetate in lavender oil, for example.

Preferred essential oils that may be mentioned include oleum eucalypti, oleum menthae piperitae, oleum camphoratum, oleum rosmarini, oleum thymi, oleum pini sibricum and oleum pini silvestris, and the terpenes 1,8-cineol and levomethanol.

Further essential oils that may be mentioned include oleum abietis albae, oleum anisi, oleum aurantii floris, oleum bargarmottae, oleum calendulae infusum, oleum camphoratum, oleum caryophylli, oleum chamomillae, oleum cinnamomi ceylanici, oleum citri, oleum citronellae, oleum cupressi, oleum cymbopogonis, oleum jecoris, oleum lavendulae, oleum macidis, oleum majoranae, oleum melaleucae viridiflorae, oleum melissae, oleum menthae arvensis, oleum menthae piperatae, oleum millefolium, oleum myrrhae, oleum myrte, oleum oregani, oleum pini sibricum, oleum pinisilvestris, oleum salviae, oleum santali, oleum terebinthinae rectificat., oleum thymi, oleum valerianae, oleum zingiberis and/or tea tree oil.

Peppermint oils are essential oils obtained by steam distillation from leaves and blossoms of various varieties of peppermint, and occasionally also those from *Mentha* arvensis.

Citrus oils are essential oils obtained from the peel of citrus fruits (bergamot, grapefruit, lime, mandarin, orange, lemon), often also called agrumen oils.

Citrus oils are composed largely of monoterpene hydrocarbons, principally limonene (exception: bergamot oil, which contains only about 40%).

Menthol can be used for example for surface anesthesia in cases of skin irritation as a result of light burns. The products used in this way generate a pleasant feeling of cold and can be used for cooling skin irritations, e.g., mild sunburn and shaving burn that do not require specialist medical treatment.

Menthol has three asymmetric C atoms and accordingly exists in four diastereomeric pairs of enantiomers (cf. the formulae; the other four enantiomers are the corresponding mirror images).

(1)

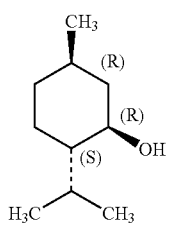

(−)-Menthol (2)

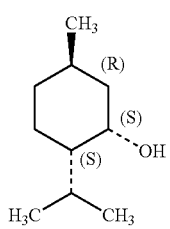

(+)-Neomenthol (3)

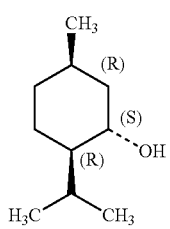

(+)-Isomenthol (4)

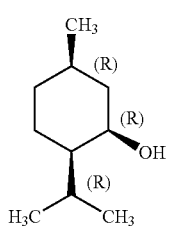

(+)-Neoisomenthol

The diastereoisomers, which can be separated by distillation, are referred to as neoisomenthol, isomenthol, neomenthol [(+) form: a constituent of Japanese peppermint oil] and menthol. The most important isomer is (−)-menthol (levomenthol), shining prisms with a strong peppermint-like odor.

As further active substances it is possible to add camphor, for example, to the matrix in order to treat skin irritations/mild pain, neuralgias and inflammation. By camphor is meant 2-bornanone, 1,7,7-trimethylbicyclo[2.2.1]heptan-2-one; see diagram below.

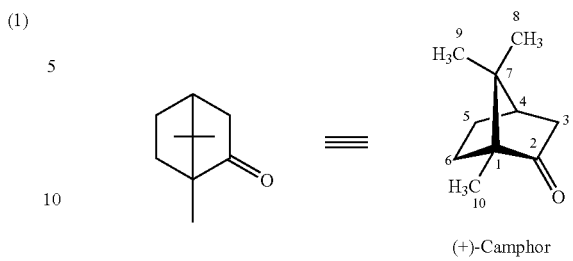

(+)-Camphor

For advantageous embodiments of hydrogels/cataplasms of the invention it is also possible, additionally, to mention active hyperemic substances such as natural active substances of cayenne pepper or synthetic active substances such as nonivamide, nicotinic acid derivatives, preferably benzyl nicotinate or propyl nicotinate, and anti-inflammatories and/or analgesics.

By way of example mention may be made of capsaicin

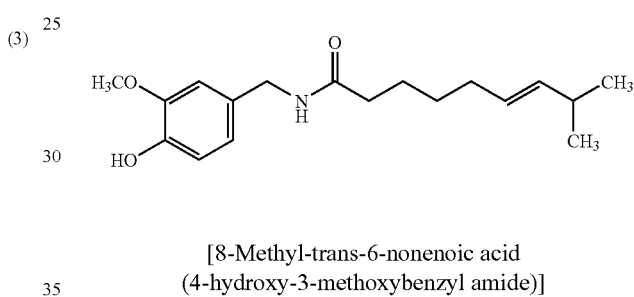

[8-Methyl-trans-6-nonenoic acid (4-hydroxy-3-methoxybenzyl amide)]

Nonivamide

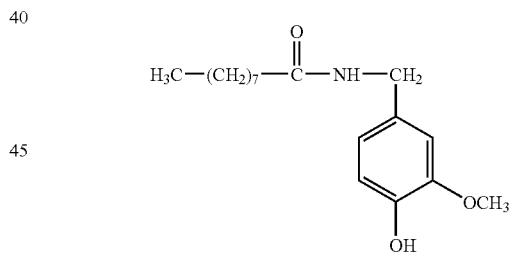

Nicotinic Acid Benzyl Ester

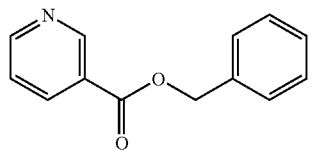

Benzyl nicotinate

Flavone and its derivatives, often also collectively called "flavones", are also advantageous additives in the sense of the present invention. They are characterized by the following basic structure (substitution positions indicated):

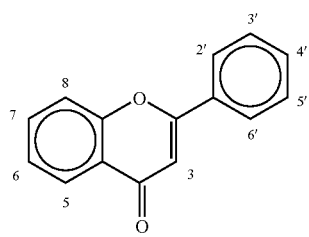

Some of the more important flavones, which can also be used with preference in preparations of the invention, are listed in the table below:

|  | OH substitution positions | | | | | | | |
|---|---|---|---|---|---|---|---|---|
|  | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kampferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones occur ordinarily in glycosylated form.

In accordance with the invention the flavonoids are preferably chosen from substances of the generic structural formula

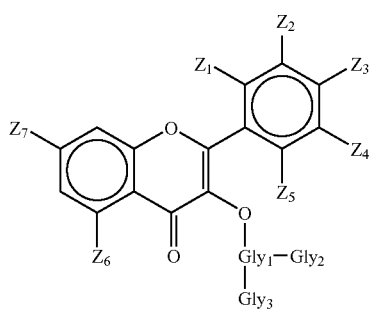

where $Z_1$ to $Z_7$ are chosen independently of one another from H, OH, alkoxy and also hydroxyalkoxy, where the alkoxy and hydroxyalkoxy groups respectively may be branched and unbranched and may have 1 to 18 C atoms, and where Gly is chosen from mono- and oligoglycoside residues.

In accordance with the invention the flavonoids can, however, also be chosen advantageously from substances of the generic structural formula

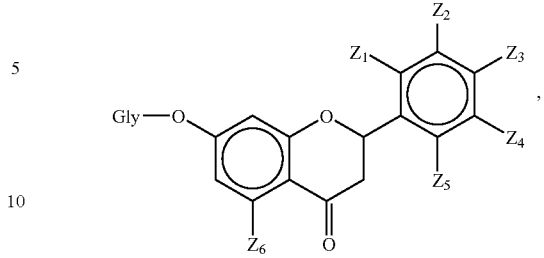

where $Z_1$ to $Z_6$ are chosen independently of one another from H, OH, alkoxy and also hydroxyalkoxy, where the alkoxy and hydroxyalkoxy groups respectively may be branched and unbranched and may have 1 to 18 C atoms, and where Gly is chosen from mono- and oligoglycoside residues.

Such structures can be chosen with preference from substances of the generic structural formula

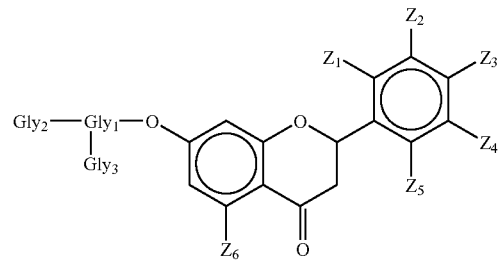

where $Gly_1$, $Gly_2$ and $Gly_3$ independently of one another represent monoglycoside residues or $Gly_2$ and/or $Gly_3$ may also, individually or together, represent saturations by hydrogen atoms.

Preferably $Gly_1$, $Gly_2$ and $Gly_3$ are chosen independently of one another from hexosyl radicals, particularly rhamnosyl radicals and glucosyl radicals. However, other hexosyl radicals can as well be used with advantage where appropriate, examples being allosyl, altrosyl, galactosyl, gulosyl, idosyl, mannosyl and talosyl. It may also be of advantage in accordance with the invention to use pentosyl radicals.

$Z_1$ to $Z_5$ advantageously are chosen independently of one another from H, OH, methoxy, ethoxy and also 2-hydroxyethoxy, and the flavone glycosides have the structure:

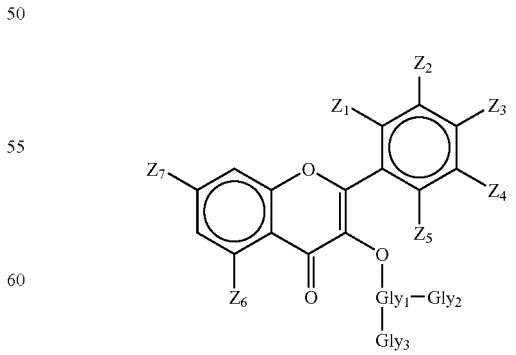

The flavone glycosides of the invention which become of particular advantage are those from the group represented by the following structure:

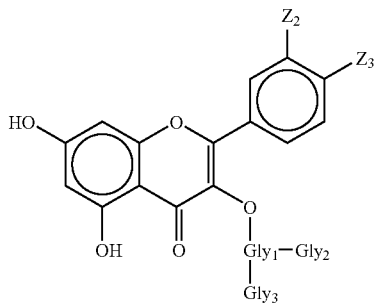

where Gly$_1$, Gly$_2$ and Gly$_3$ independently of one another represent monoglycoside residues or oligoglycoside residues. Gly$_2$ and/or Gly$_3$ may also, individually or together, represent saturations by hydrogen atoms.

Preferably Gly$_1$, Gly$_2$ and Gly$_3$ independently of one another are chosen from hexosyl radicals, in particular rhamnosyl radicals and glucosyl radicals. However, other hexosyl radicals can as well be used with advantage where appropriate, examples being allosyl, altrosyl, galactosyl, gulosyl, idosyl, mannosyl and tallosyl. It may also be an advantage in accordance with the invention to use pentosyl radicals.

In the sense of the present invention it is particularly advantageous to choose the flavone glycoside or glycosides from α-glucosylrutin, α-glucosylmyricetin, α-glucosylisoquercitrin, α-glucosylisoquercetin and α-glucosylquercitrin.

Of particular preference in accordance with the invention is α-glucosylrutin.

Also advantageous in accordance with the invention are naringin (aurantiin, naringenin 7-rhamnoglucoside), hesperidin (3',5,7-trihydroxy-4'-methoxyflavanone 7-rutinoside, hesperidoside, hesperetin 7-O-rutinoside), rutin (3,3',4',5,7-pentahydroxyflyvone 3-rutinoside, quercetin 3-rutinoside, sophorin, birutan, rutabion, taurutin, phytomelin, melin), troxerutin (3,5-dihydroxy-3',4',7-tris(2-hydroxyethoxy)flavone 3-(6-(O-(6-deoxy-α-L-mannopyranosyl)-β-D-glucopyranoside)), monoxerutin (3,3',4',5-tetrahydroxy-7-(2-hydroxyethoxy)flavone 3-(6-(O-(6-deoxy-α-L-mannopyranosyl)-β-D-glucopyranoside)), dihydrorobinetin (3,3',4',5',7-pentahydroxyflavonone), taxifolin (3,3',4',5,7-penta-hydroxyflavanone), eriodictyol-7-glucoside (3',4',5,7-tetrahydroxyflavanone 7-glucoside), flavanomarein (3',4',7,8-tetrahydroxyflavanone 7-glucoside) and isoquercetin (3,3',4',5,7-pentahydroxyflavanone-3-(β-D-glucopyranoside)) or derivatives thereof.

Further preferred classes of active substance for a gel matrix of the invention include the following—without making any claim to completeness in the context of the present invention:

antimycotics, such as nafitine, amorrolfine, tolnaftate, ciclopirox nonsteroidal antiinflammatories, such as glycol salicylate, flufenamic acid, ibuprofen, etofenamate, ketoprofen, piroxicam, indomethacin anti-inflammatories, such as acetylsalicylic acid antipruritics, such as polidocanol, isoprenaline, crotamiton local anesthetics, such as lidocaine, benzocaine antipsoriatics, such as ammonium bitumasulfonate keratolytics, such as urea Among the active substances, those which should be emphasized as being particularly important for polymer matrices, hydrogels/cataplasms or cosmetic pads of the invention are the disinfectants or antiseptics.

Substances designated as disinfectants are those suitable for disinfection, i.e., for controlling pathogenic microorganisms, such as bacteria, viruses, spores, microfungi and molds. In general the products are employed on the surface of skin, clothing, equipment, rooms, but also drinking water, foodstuffs, seeds (dressing) and as soil disinfectants.

Disinfectants particularly for local application, such as for wound disinfection, for example, are also referred to as antiseptics.

Disinfectants are defined as substances or compositions which, when used on articles or surfaces, place them in such a condition that they no longer cause any infection. Their action must be bactericidal, fungicidal, virucidal and sporicidal, i.e., the collective term: microbicidal. A bacteriostatic effect is inadequate for disinfectants. In general, therefore, they are pantoxic, i.e., they develop their action against all living cells.

Depending on the intended use, the disinfectants are divided into those for disinfecting laundry, surfaces, instruments, skin and hands, and for stool and sputum disinfection. Disinfectant cleaners are understood as being those disinfectants which also act as cleaning products and, where appropriate, care products.

Taking into account the diverse requirements imposed on disinfectants, such as, for example, broad-spectrum action, short activity times, skin compatibility, low toxicity, materials compatibility, and so on, only certain types of active substance are suitable for the desired use.

1. The most important group of active substances are the aldehydes (formaldehyde, glyoxal, glutaraldehyde). They possess a broad-spectrum action including virus activity and sporicidal action in the case of formaldehyde and glutaraldehyde.

2. Phenol derivatives possess a good bactericidal action, but are not sporicidal. Compared with almost all other active disinfectant substances, they have the advantage of being relatively unaffected by dirt. They are therefore particularly suitable for stool disinfection. Typical representatives are 2-biphenylol and p-chloro-m-cresol (4-chloro-3-methylphenol).

3. Alcohols are distinguished by rapid activity, but only at relatively high concentrations of about 40%-80%.

4. The quaternary ammonium compounds, cationic surfactants (invert soaps) and amphoteric surfactants belong to the class of the surfactants. They are characterized by fairly good skin compatibility and materials compatibility and also by odor neutrality. Their spectrum of action, however, is only limited. They include, for example, benzalkonium chloride, cetrimonium bromide, cetylpyridinium chloride (hexadecylpyridinium chloride) and others.

Quaternary ammonium compounds are organic ammonium compounds containing quaternary nitrogen atoms. Quaternary ammonium compounds having a hydrophobic alkyl radical are biocidal; their use is admittedly declining, for toxicological reasons.

Quaternary ammonium compounds are prepared by reacting tertiary amines with alkylating agents, such as methyl chloride, benzyl chloride, dimethyl sulfate, dodecyl bromide, for example, but also ethylene oxide. Depending on the tertiary amine employed, three groups are differentiated:

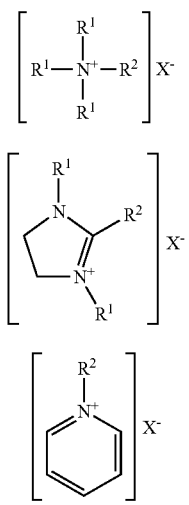

a) linear alkylammonium compounds
b) imidazolinium compounds
c) pyridinium compounds $R^1$=$CH_3$, $R^2$=$C_{8-18}$, X=halogen.

The alkylation of tertiary amines having a long alkyl radical and two methyl groups is accomplished particularly easily, and the quaternization of tertiary amines having two long radicals and one methyl group can be carried out using methyl chloride under mild conditions. Amines possessing three long alkyl radicals or hydroxy-substituted alkyl radicals are not very reactive and are preferably quaternized using dimethyl sulfate.

5. Among the halogens, chlorine and iodine possess a certain significance as disinfectants. Chlorine is known from water treatment and pool disinfection and, therewith, its unpleasant properties such as odor and corrosiveness. In spite of the excellent action against bacteria, fungi, spores and viruses, chlorine-containing disinfectants have not found any great use in the human segment, for the abovementioned reasons and on account of the heavy chlorine loss due to organic substances. In contrast, hypochlorites, chloride of lime and chloroisocyanuric acids are still used extensively as industrial disinfectants. Tincture of iodine is used in the medical segment as an antiseptic.
6. Disinfectants based on active oxygen (for example, hydrogen peroxide, peroxyacetic acid) have recently regained some importance.
7. Silver, both alone and in bound form, has a strongly antiseptic action, since the Ag ions contained in the oxide layer of the metal surface exert a blocking effect on the thiol enzymes in the microorganisms. Ag ions are also strongly fungicidal and bactericidal. Thin, bactericidal silver foils are therefore used as a wound dressing material, likewise silver aerosols, silver solutions, silver-containing ointments, tablets and the like as antiseptics and antimycotics.

The silver ions can be used in the form of salts, zeolites, e.g., aluminum silicates, or, preferably, silver glasses.

Aside from the stated active microbicidal substances, a number of microbistatic substances and preservatives (diphenyl ether, carbanilides, acetanilides of aromatic acids and salts thereof) are still on the market for specific use, and are included among disinfectants in the broader sense.

No uniform mode of action of the disinfectants can be discerned. While certain preparations are supposed to act destructively on the cytoplasmic membrane of the bacteria, for others an irreversible blocking of important sulfide bonds in enzymes or of trace elements, by chelation, is assumed.

The invention accordingly further provides for the use of disinfectant products in polymer matrices which comprise
  at least one nonionic surfactant and
  at least one amino acid and/or amino acid derivative
  and at least one disinfectant agent and/or active microbicidal substance.

The nonionic surfactant or surfactants is or are chosen advantageously from alkyl ethoxylates and/or alkyl propoxylates whose alkyl group is a saturated or unsaturated, straight- or branched-chain alkyl group having (8) 10 to 18, preferably 12 to 14, carbon atoms; they preferably contain per molecule 2 to 15, in particular 5 to 9, and especially 7 ethylene oxide units. Very particular preference is given to isotridecanol ethoxylate and/or fatty alcohol polyglycol ethers.

Advantageously the total amount of nonionic surfactants (one or more compounds) is chosen from the range from 1.0% to 20.0% by weight, preferably from 5.0% to 15.0% by weight, based in each case on the total weight of the matrix.

Advantageous amino acids are, for example, glutamic acid, which is characterized by the following structural formula:

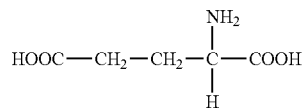

and/or pyrrolidone carboxylic acid (pyroglutamic acid), which is characterized by the following structural formula:

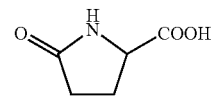

Advantageously the total amount of amino acids (one or more compounds) is chosen from the range from 0.1% to 10.0% by weight, preferably from 0.5% to 2.0% by weight, based in each case on the total weight of the matrix.

The disinfectant agent or agents (active microbicidal substances) are preferably chosen from aldehydes (for example, formaldehyde, glyoxal, glutaraldehyde), phenol derivatives (for example, 2-biphenylol and p-chloro-m-cresol (4-chloro-3-methylphenol)), alcohols, quaternary ammonium compounds (for example, benzalkonium chloride, cetrimonium bromide, cetylpyridinium chloride (hexadecylpyridinium chloride). Aldehydes and quaternary ammonium compounds are especially preferred in this context.

In one particularly advantageous embodiment the disinfectant systems may further comprise amphoteric surfactants. Amphoteric surfactants are surfactants which possess both acidic and basic hydrophilic groups and which therefore, depending on conditions, behave acidically or basically. Advantageous are, for example, amphoteric surfactants based on aliphatic polyamines having carboxyl, sulfo or phosphono side chains, such as R—NH—$(CH_2)_n$—COOH, for example.

Preference is given for example to amphoteric surfactants whose alkyl group is a saturated or unsaturated, straight- or branched-chain alkyl group having 10 to 18, preferably 12 to 14, carbon atoms.

Further of particular advantage are amphoteric surfactants from the group of the amphopropionates, such as, for example, cocobetaineamido amphopropionate, which is characterized by the following structure:

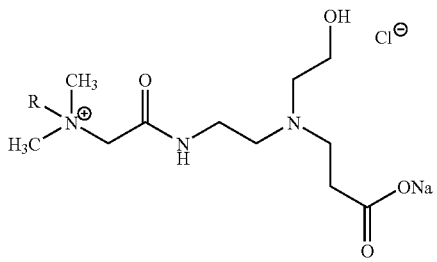

The total amount of amphoteric surfactants (one or more compounds) is advantageously chosen from the range from 1.0% to 10.0% by weight, preferably from 2.0% to 5.0% by weight, based in each case on the total weight of the matrix.

It is advantageous to carry out dilution such that the amount of the individual substances in the solution for use is as follows:

| | |
|---|---|
| nonionic surfactants: | between 0.005% and 1% by weight |
| amino acid: | between 0.0005% and 0.5% by weight |
| optionally, amphoteric surfactants: | between 0.005% and 0.5% by weight |
| disinfectant agents: | between 0.01% and 2.0% by weight |

In addition to the components specified above, the disinfectant systems for such preparations may comprise customary preservatives, dyes, fragrances and/or other customary auxiliaries. It is also possible, however, to use components which develop a (preserving, caring, etc.) action and at the same time provide a certain color and/or a pleasant fragrance.

The amounts of such vehicles and perfume to be employed in each case can be determined easily as a function of the nature of the specific product by the skilled worker, by simple trial.

Also of advantage is the use of disinfectant systems which comprise at least one active microbicidal substance chosen from alkylamines, at least one amino acid and/or amino acid derivative, and at least one quaternary ammonium compound.

With advantage the quaternary ammonium compounds are preferably chosen from benzalkonium chloride, didecyldimethylammonium chloride, cetrimonium bromide and cetylpyridinium chloride (hexadecylpyridinium chloride). The alkylamine is advantageously dodecylbispropylenetriamine.

In accordance with the invention, advantageously, nonionic surfactants are additionally added, chosen with particular advantage from alkyl ethoxylates whose alkyl group is a saturated or unsaturated, straight- or branched-chain alkyl group having 8 to 18, preferably 12 to 14, carbon atoms, and containing preferably per molecule 2 to 15, in particular 5 to 9, especially 7, ethylene oxide units. Very particular preference is given to isotridecanol ethoxylate and/or fatty alcohol polyglycol ethers.

The total amount of nonionic surfactants (one or more compounds) is advantageously chosen from the range from 1.0% to 20.0% by weight, preferably from 5.0% to 15.0% by weight, based in each case on the total weight of the matrix.

Additionally, as agents for disinfection, preservation and antisepsis, a multiplicity of microbicidally active chemical substances or mixtures of these substances is known per se. Microbicidal substances are in general active against the customary spectrum of microorganisms, such as gram-positive bacteria, gram-negative bacteria, mycobacteria, yeasts, fungi, viruses and the like, for example, to a greater or lesser extent, and so normally sufficient disinfection, preservation or antisepsis can be achieved by means of suitable active-substance combinations.

For the purpose of disinfection, preservation and antisepsis a range of active substances are known, especially aldehydes, such as formaldehyde or glutaraldehyde, for example, quaternary ammonium compounds and long-chain amines, phenols or alcohols.

Aldehydes fix residues of blood and protein by means of chemical reaction on the articles to be disinfected, so that following disinfection these articles are difficult to clean. Moreover, they have a comparatively high allergenic potential, and so applications to skin and hands are possible only in low concentrations or else can be contemplated in combination with further active substances, in order to be able to remain—as required—below the sensitization threshold. Higher concentrations of aldehydes are also undesirable on account of their odor, and for this reason as well the concentration is reduced by combination with further active substances.

Quaternary ammonium compounds and long-chain amines are frequently used in surface disinfection and for manual instrument disinfection and to a small extent also in antisepsis of the hands. In comparison to the aldehydes, the odor of these compounds is significantly less unpleasant. There is no chemical reaction with proteins, but there is a physical precipitation of proteins, which can be partially compensated by skillful combination with surfactants. For mechanical disinfection of instruments the quaternary ammonium compounds are not suitable, since owing to the turbulences within the cleaning machine there is severe, unwanted foaming. In the case of surface disinfection, quaternary ammonium compounds show a strong tendency to "attach" to the surfaces; that is, layers of these compounds are developed on the surfaces. A further crucial disadvantage is the restricted spectrum of action of quaternary ammonium compounds, since they act neither sporicidally nor against non-enveloped viruses.

Phenols are on the decline principally on account of their odor, their low level of activity against the polio virus, their in some cases poor degradability, their high lipid solubility in conjunction with strong penetration through the skin, and also toxicology and mutagenicity risks, in virtually all segments of application for disinfectants.

The aliphatic alcohols ethanol, propan-1-ol and propan-2-ol have long been known as active substances for disinfecting skin and hands or for the antisepsis of skin and hands. With disinfectants and antiseptics based on alcohols it is possible with short exposure times of 30 to 60 seconds to obtain germ count reductions of up to 99.9%. A general, brief presentation of the microbicidal activity of alcohols is found in the following book: K. H. Wallhäußer, "*Praxis der Sterilisation, Desinfektion und Konservierung*" G. Thieme Verlag, Stuttgart, N.Y., 5th edition, pp. 469-474.

Alcohols possess a bactericidal action which increases from methanol to propanol. Use is made in particular of ethanol, n-propanol and isopropanol, the alcohol content of the preparations being situated generally between 50% and 80%. The essential advantage of alcohols is that the onset of action is very rapid. Disadvantages are that they are not active against spores and that the action ends after a very short time, since alcohols evaporate rapidly. Although an antiviral activity is under discussion for alcohols, it is only on the other side of a high concentration limit, which in the case of ethanol is presumed to be about 80%.

It has been found in practice that alcoholic disinfectants and antiseptics are unable, or unable adequately, to destroy viruses and traces of *Bacillus* and *Clostridium* species. Although the freedom of alcoholic solutions from spores can be achieved by filtration, it cannot be completely ruled out in practice that microorganism spores will (subsequently) enter the preparations, for example, during the brief opening of the storage vessels or during dispensing of the products into containers already containing spores. For this reason, when using alcoholic skin and hand antiseptics, there is always a certain risk of an infection caused by spores.

Antiseptics are particularly suitable for treating the skin. Antiseptics display a very good activity against dermatophytes and in particular are characterized, surprisingly, by the fact that they have a very good activity with respect to viruses.

The constituents of antiseptics act synergistically in respect of their antimicrobial and antiviral properties, i.e., act super-additively in a significant way.

Also advantageous, accordingly, is the use of a preparation comprising

| | |
|---|---|
| (a) 42%-47% by weight | of 1-propanol |
| (b) 22%-27% by weight | of 2-propanol |
| (C) 4%-6% by weight | of ethanol |
| (d) at least 20% by weight | of water |
| (e) not more than 0.0001% by weight | of substances which under standard conditions are in the form of solids |
| (f) no effective content | of further substances which are characterized by virucidal properties | as an antiseptic, particularly its use for controlling or inactivating the HIV virus or the hepatitis B virus.

Particularly suitable as an antiseptic is, in turn, chlorohexidine,

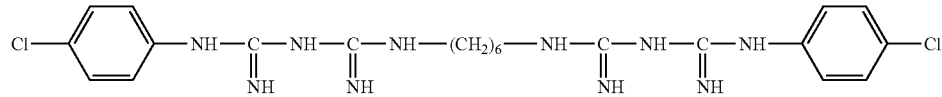

the international nonproprietary name for 1,1'-hexamethylenebis[5-(4-chloro-phenyl)biguanide], the antiseptic used being the dihydrochloride, diacetate and digluconate.

For use as patches or cosmetic matrix/cosmetic pad, the gel matrices of the invention are pressed, rolled or the like as a layer onto a release medium made of paper, film or the like and are laminated on the reverse with any desired backing material such as, for example, a polymer film, textiles or the like. With particular preference in accordance with the invention the gel matrices are applied in the hot state by a metering pump to a backing material, and with very particular preference are configured in a three-dimensional form by means of corresponding cavities in the presses or roller mechanisms. The shape of the patches or cosmetic matrix produced is determined by the shape of the cavities and is not subject to any restriction; it may, for example, be ellipsoidal with edges which flatten off, or may, for example, be angular in configuration.

With particular advantage the gel matrix of the invention is applied on a flexible cover layer, particularly when used as a patch/cosmetic matrix. A corresponding patch/a corresponding cosmetic matrix is constructed from a backing such as films, nonwovens, wovens, foams, etc., the adhesive matrix, and liner film, liner paper or release paper in order to protect the adhesive matrix prior to the use of the patch/the cosmetic matrix.

In a further preferred embodiment of the invention, backings used are polymer films, nonwovens, wovens and combinations thereof. Backing materials available for selection include polymers such as polyethylene, polypropylene, polyesters, polyethers, polyether-ester copolymers and polyurethane or else natural fibers.

In summary it can be stated that suitable backing materials encompass all rigid and elastic sheet-like structures of synthetic and natural raw materials. Preference is given to backing materials which can be employed such that they fulfill properties of a functional dressing. Listed by way of example are textiles such as wovens, knits, lays, nonwovens, laminates, nets, films, foams and papers. In addition it is also possible for these materials to be pretreated and/or aftertreated. Customary pretreatments are corona and hydrophobicization; common after-treatments are calendering, heat-treating, laminating, punching and enveloping.

It is particularly advantageous if the backing material is sterilizable, preferably γ(gamma)-sterilizable.

Very particularly preferred backing materials in accordance with the invention are those which have good oxygen, air and water vapor permeability, which have been provided point-wise with strongly adhesive polymers such as polyisobutylene, SEBS block polymers, natural rubbers and/or synthetic rubbers, polyurethane or the like by screen printing or analogous methods, and which outwardly overlap the applied hydrogel matrix at the side edges. Matrices of the invention manufactured in this form can be affixed self-adhesively to parts of the body that are under severe mechanical stress, such as elbows or knee joints, where the inherent adhesion of the hydrogels/cataplasms is no longer sufficient for durable application.

The stated properties of the adhesive matrix suggest its use in particular for medical products, especially patches, medical fastenings, wound coverings, orthopedic or phlebological bandages, and dressings. Use as a cosmetic or dermatological pad is very particularly preferred.

Finally the gel matrix can be enveloped with an anti-adhesive backing material, such as siliconized paper, or provided with a wound pad or a cushion. On its self-adhesive side which later faces the skin, the cosmetic matrix of the invention is lined over its whole width, until used, usually with an anti-adhesive backing material. This protects the self-adhesive layer from the gel matrix's adhesive, which possesses good skin compatibility and which has preferably been applied by a transfer method, and additionally stabilizes the product as a whole. The lining can be designed, in a known way, in once piece or, preferably, in two parts.

Further embodiments may be such that between the reverse of the matrix and the lining backing there is a second matrix possessing higher active-substance solubility, as a reservoir. Instead of a second matrix and backing, this might also be a thermoformed film with pure active substance.

Located on part (e.g., at the edge) of the adhesive side of the matrix is a second matrix possessing high bond strength for the purpose of additional fixing, but possessing insufficient active-substance solubility.

The active substance-free matrix is located between two non-anchoring films and is utilized for fixing.

The present invention further provides for the use of active cosmetic or dermatological substances in the gel matrices of the invention.

In particular the use of the active-substance-doped gel matrices based on polyacrylic acid/agar-agar for use as PADs for the cosmetic and beneficial treatment of unwanted skin phenomena is to be emphasized with preference. Particularly in connection with the treatment of skin aging phenomena, especially wrinkles, in pigmentation disorders, particularly age spots, and inflammatory/irritative skin phenomena, such as in the case of shaving burn and/or sunburn, for example.

It is preferred in the sense of the present invention if the cosmetic or dermatological matrices of the invention further comprise one or more alcohols, particularly if the formulations are in the form of an aftersun product and are to be characterized by a particular cooling effect.

The use of the polymer matrix as cosmetic or dermatological pads or plasters is suitable particularly in a flat embodiment with a total area of 0.2 to 1000 cm². With this, for example, small (0.2-2 cm²) regions of the skin or large regions (up to 1000 cm²) are covered for the purpose of intensive cooling.

Preference is given to the use of the self-adhesive polymer matrix in two- or three-dimensional embodiment with a polymer matrix weight fraction of 0.1 to 1000 g, in particular of 500 g. The shape in this case may be round, oval, angular or designed in accordance with the sections of the skin.

DETAILED DESCRIPTION OF THE INVENTION

The examples which follow illustrate the invention without restricting it. The tables below list gel matrices of the invention. The mass fractions reported are based on the overall mass of the matrix.

Examples I-III

| Constituent | I | II | III |
|---|---|---|---|
| Water | ad 100% | ad 100% | ad 100% |
| Agar-agar | 2.0% | 2.0% | 2.0% |
| Glycerin | 20.0% | 30.0% | 40.0% |
| Liquorice extract | 0.1% | 0.1% | 0.1% |
| Carbopol 980 | 8.0% | 8.0% | 8.0% |
| NaOH | 0.1% | 0.1% | 0.1% |

Examples I-III exhibit similar adhesion with a constant polyacrylic acid content and with a likewise constant agar-agar content, but increasing cohesiveness/elasticity with increasing glycerin content.

Examples IV-VI

| Constituent | IV | V | VI |
|---|---|---|---|
| Water | ad 100% | ad 100% | Ad 100% |
| Agar-agar | 2.0% | 2.0% | 2.0% |
| Liponamide | 0.1% | 0.05% | 0.1% |
| Glycerin | 30.0% | 30.0% | 30.0% |
| Carbopol 980 | 8.0% | 12.0% | 16.0% |
| NaOH | 0.1% | 0.1% | 0.1% |

Examples IV-VI exhibit analogous cohesiveness/elasticity with a constant agar-agar and glycerin content and increasing adhesion with a simultaneously increasing polyacrylic acid content.

Examples VII-IX

| Constituent | VII | VIII | IX |
|---|---|---|---|
| Water | ad 100% | ad 100% | ad 100% |
| Sorbitol | 15.7% | 15.0% | 15.7% |
| Agar-agar | 2.0% | 2.0% | 2.0% |
| Glycerin | 15.0% | 15.0% | 15.0% |
| Carbopol 980 | 8.0% | 8.0% | 8.0% |
| Creatin | 0.2% | 0.25% | 0.1% |
| NaOH | 0.1% | 0.1% | 0.1% |
| Propanediol | 5.0% | — | — |
| Menthol | 1.0% | — | — |
| Dexpanthenol | 1.0% | — | — |
| Capsicum extract | — | 3.0% | — |
| Chlorhexidine digluconate | — | — | 1.0% |

In every respect the formulations of the invention are completely satisfactory preparations which are characterized by an outstanding action. When the active substances used in accordance with the invention or cosmetic or topical dermatological preparations are used with an effective content of active substances used in accordance with the invention it is possible to achieve effective treatment, but also prophylaxis, of inflammatory skin conditions—including atopic eczema—and/or skin protection in the case of dry skin which has been determined as being sensitive. The active substance of the invention or cosmetic or topical dermatological preparations containing an effective amount of active substance of the invention also serve surprisingly, however, for soothing sensitive or irritated skin.

The following preparations have proved to be particularly suitable for use for age spots:

Examples X-XII

| Constituent | X | XI | XII |
|---|---|---|---|
| Water | ad 100% | ad 100% | ad 100% |
| Sorbitol | 15.7% | 15.7% | 15.7% |

-continued

| Constituent | X | XI | XII |
|---|---|---|---|
| Agar-agar | 2.0% | 2.0% | 2.0% |
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Creatine | — | — | 0.5% |
| Liponamide | 0.05% | 0.1% | — |

The following preparations have proved to be particularly suitable for use for inflammatory and irritative skin conditions, in particular for shaving burn and sunburn:

Examples XIII-XV

| Constituent | XIII | XIV | XV |
|---|---|---|---|
| Water | ad 100% | ad 100% | ad 100% |
| Sorbitol | 15.7% | 15.7% | 15.7% |
| Agar-agar | 2.0% | 2.0% | 2.0% |
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Liquorice extract | 0.01% | 0.05% | — |

The following preparations have proved to be particularly suitable for use for age-related wrinkles:

Examples XVI-XVIII

| Constituent | XVI | XVII | XVIII |
|---|---|---|---|
| Water | ad 100% | ad 100% | ad 100% |
| Sorbitol | 15.7% | 15.7% | 15.7% |
| Agar-agar | 2.0% | 2.0% | 2.0% |
| Propanediol | 5.0% | 5.0% | 5.0% |
| Glycerin | 15.0% | 15.0% | 15.0% |
| Carbopol 980 | 8.0% | 8.0% | 8.0% |
| NaOH | 0.1% | 0.1% | 0.1% |
| Q10 | — | — | 0.1% |
| Creatine | 0.5% | 0.1% | — |

What is claimed is:

1. A polymer matrix, wherein the polymer matrix is self-adhesive and comprises from 2% to 30% by weight of (a) at least one polymer which forms a gel in water, (b) water, from 0.1% to 15% by weight of (c) a sea algae extract, and from 1% to 85% by weight of (d) at least one alcohol selected from monohydric and polyhydric alcohols which comprises glycerin, each based on a total weight of the matrix.

2. The polymer matrix of claim 1, wherein the matrix comprises at least 5% of (a), from 0.5% to 5% by weight of (c), and from 5% to 45% by weight of (d).

3. The polymer matrix of claim 2, wherein (a) comprises at least one polyacrylic acid polymer, and (c) comprises at least one of agar-agar and carrageenan.

4. The polymer matrix of claim 1, wherein (d) further comprises at least one of propanediol and sorbitol.

5. The polymer matrix of claim 2, wherein (d) further comprises at least propanediol.

6. The polymer matrix of claim 2, wherein (c) comprises agar-agar.

7. The polymer matrix of claim 1, wherein the matrix comprises at least 15.0% by weight of glycerin, based on a total weight of the matrix.

8. The polymer matrix of claim 1, wherein the matrix further comprises from 0.02% to 35% by weight of (e) at least one dermatological or cosmetic active substance, based on a total weight of the matrix.

9. The polymer matrix of claim 8, wherein (e) comprises at least one of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera.

10. The polymer matrix of claim 8, wherein (e) comprises at least one substance selected from disinfectants and antiseptics.

11. The polymer matrix of claim 8, wherein the matrix comprises not more than 15% by weight of (e).

12. The polymer matrix of claim 11, wherein the matrix comprises not more than 2% by weight of (e).

13. A polymer matrix, wherein the polymer matrix is self-adhesive and comprises from 5% to 30% by weight of (a) at least one polymer which forms a gel in water and comprises at least one polyacrylic acid polymer, (b) water, from 0.5% to 5% by weight of (c) a sea algae extract which comprises agar-agar, from 15% to 45% by weight of (d) one or more monohydric or polyhydric alcohols which comprise at least 15% by weight of glycerol, and from 0.02% to 2% by weight of (e) at least one dermatological or cosmetic active substance, each based on a total weight of the matrix.

14. The polymer matrix of claim 13, wherein the at least one polyacrylic acid polymer comprises an acrylate-alkyl acrylate copolymer having the structure:

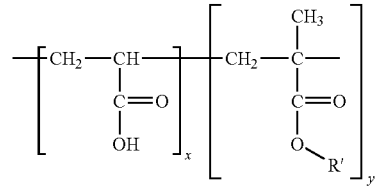

where R' is an alkyl radical and x and y indicate the stoichiometric fraction of the respective comonomers.

15. The polymer matrix of claim 13, wherein the at least one polyacrylic acid polymer comprises a copolymer of a $C_{10-30}$ alkyl acrylate and one or more of acrylic acid, methacrylic acid and esters thereof, which copolymer is crosslinked with an allyl ether of sucrose or with an allyl ether of pentaerythritol.

16. The polymer matrix of claim 13, wherein (e) comprises at least one of creatine, creatinine, alpha-glucosylrutin, taurine, serinol, isoserinol, liquorice aqua PU, liquorice PU, silymarin, silyphos, lipoic acid, liponamide, green tea extract, vitamin C, 8-hexadecene-1,16-dicarboxylic acid, isoflavone, isoflavonoid-containing plant extracts, ubiquinone Q10, sericosides, tyrosine sulfate, jojoba oil, and aloe vera.

17. The polymer matrix of claim 13, wherein (e) comprises at least one substance selected from disinfectants and antiseptics.

18. A patch, a cosmetic or dermatological matrix or a pad which comprises the polymer matrix of claim 1.

19. A two-dimensional product which comprises the polymer matrix of claim 1 and has a total area of from 0.2 to 1000 cm².

20. A two-dimensional or three-dimensional product which comprises from 0.1 to 1,000 g of the polymer matrix of claim 1.

21. The polymer matrix of claim 1, wherein the matrix is present on a backing material.

22. The polymer matrix of claim 13, wherein the matrix is present on a backing material.

* * * * *